US007998475B2

(12) United States Patent
Alphey

(10) Patent No.: US 7,998,475 B2
(45) Date of Patent: Aug. 16, 2011

(54) DILUTION OF GENETIC TRAITS

(75) Inventor: Luke Alphey, Abingdon (GB)

(73) Assignee: Oxitec Limited, Oxford (GB)

( * ) Notice: Subject to any disclaimer, the term of this patent is extended or adjusted under 35 U.S.C. 154(b) by 1445 days.

(21) Appl. No.: 10/556,804

(22) PCT Filed: May 12, 2004

(86) PCT No.: PCT/GB2004/002021
§ 371 (c)(1),
(2), (4) Date: Jan. 18, 2006

(87) PCT Pub. No.: WO2004/098278
PCT Pub. Date: Nov. 18, 2004

(65) Prior Publication Data
US 2006/0275276 A1 Dec. 7, 2006

(30) Foreign Application Priority Data

May 12, 2003 (GB) .................................. 0310880.0

(51) Int. Cl.
*A01K 67/033* (2006.01)
*A01N 63/00* (2006.01)
(52) U.S. Cl. .................................... 424/93.461; 800/13
(58) Field of Classification Search .................. None
See application file for complete search history.

(56) References Cited

U.S. PATENT DOCUMENTS

| | | | |
|---|---|---|---|
| 5,254,801 A | 10/1993 | Dotson et al. | |
| 5,851,796 A * | 12/1998 | Schatz | |
| 6,200,800 B1 * | 3/2001 | Choulika et al. | |
| 6,338,040 B1 * | 1/2002 | Buman et al. | 705/4 |
| 6,962,810 B2 * | 11/2005 | Fraser et al. | |
| 2003/0150007 A1 * | 8/2003 | Savakis et al. | |
| 2003/0213005 A1 * | 11/2003 | Alphey et al. | |
| 2004/0082032 A1 * | 4/2004 | Bovi et al. | |
| 2005/0221430 A1 * | 10/2005 | Prentice | |
| 2006/0212949 A1 * | 9/2006 | Alphey | |
| 2006/0242717 A1 * | 10/2006 | Alphey | |
| 2006/0275276 A1 * | 12/2006 | Alphey | 424/93.461 |
| 2007/0056051 A1 * | 3/2007 | Alphey | |
| 2008/0115233 A1 * | 5/2008 | Alphey et al. | |
| 2009/0170793 A1 * | 7/2009 | Gaur | |
| 2009/0183269 A1 * | 7/2009 | Alphey | |

FOREIGN PATENT DOCUMENTS

| | | | |
|---|---|---|---|
| EP | 0955364 | * | 11/1999 |
| GB | 2 355 459 | | 4/2001 |
| WO | 96/24605 | * | 8/1996 |
| WO | 98/08960 | * | 3/1998 |
| WO | 00/73510 | * | 12/2000 |
| WO | WO 01/39599 | | 6/2001 |
| WO | 01/59088 | * | 8/2001 |
| WO | 01/91802 | * | 12/2001 |
| WO | 02/46444 | * | 6/2002 |
| WO | 02/101061 | * | 12/2002 |
| WO | 2004/044150 | * | 5/2004 |
| WO | 2004/098278 | * | 11/2004 |
| WO | 2005/003364 | * | 1/2005 |
| WO | 2005/012534 | * | 2/2005 |
| WO | 2007/091099 | * | 8/2007 |

OTHER PUBLICATIONS

Alphey et al. (Journal of Economic Entomology. 2007; 100 (5): 1642-1649).*
Fu et al. (Nature Biotechnology. 2007; 25 (3): 353-357).*
Alphey et al. (May 2002) "Dominant Lethality and Insect Population Control," *Mol. Biochem. Parasit.* 121(2):173-178.
Carriere et al. (2001) "Reversing Insect Adaptation to Transgenic Insecticidal Plants," *Proc. Roy. Soc. (Lond) B.* 268:1475-1480.
Davis et al. (Sep. 2001) "Engineered Underdominance Allows Efficient and Economical Introgression of Traits into Pest Populations," *J. Theor. Biol.* 212(1):83-98.
Heinrich et al. (2000) "A Repressible Female-Specific Lethal Genetic System for Making Transgenic Insect Strains Suitable for a Sterile-Release Program," *Proc. Nat. Acad. Sci. USA* 97(15):8229-8232.
Horn et al. (Jan. 2003) "A Transgene-Based, Embryo-Specific Lethality Sysytem for Insect Pest Management," *Nature Biotech.* 21:64-70.
Robinson et al. (Jun. 2002) "Mutations and Their Use in Insect Control," *Mutat. Res.* 511(2):113-132.
Shelton et al. (Mar. 2000) "Field Tests on Managing Resistance to Bt-Engineered Plants," *Nat. Biotechnol.* 18(3):339-342.
Thomas et al. (2000) "Insect Population Control Using a Dominant, Repressible Lethal Genetic System," *Science* 287:2474-2476.
Imai (1987) "Control of Insecticide Resistance in a Field Population of Houseflies, *Musca domestica*, by Releasing Susceptible Flies," *Res. Popul. Ecol.* 29, 129-146.
Wool et al. (1980) "Genetically-Induced Susceptibility to Malathion in *Tribolium castaneum* Despite Selection for Resistance," *Ent. Exp. & Appl.* 28, 183-190.
Examination Report for European patent application serial No. 04743590.4, dated Nov. 14, 2008, 4 pages.
Search Report Corresponding to Great Britain Patent Application No. GB 0317656.7, Date of Search Nov. 25, 2003, 1 page.
Search Report Corresponding to Great Britain Patent Application No. GB 0621234.4, Date of Search Feb. 21, 2007, 1 page.
Search Report Corresponding to International Application No. PCT/GB2004/003263, Date of search Oct. 21, 2004, Mailed May 11, 2004, 3 pages.
Search Report corresponding to International Application No. PCT/GB2007/000488, parent of the present application, Date of search May 11, 2007, Date of mailing Jun. 6, 2007, 3 pages.
Written Opinion corresponding to International Application No. PCT/GB2007/000488, parent of the present application. Date according to WIPO website Aug. 10, 2008, 8 pages.
International Preliminary Report on Patentability, corresponding to International Application No. PCT/GB2007/000488, parent of the present application, Date of completion of report May 5, 2008, 11 pages.

(Continued)

*Primary Examiner* — Shanon A Foley
(74) *Attorney, Agent, or Firm* — Greenlee Sullivan P.C.

(57) ABSTRACT

Undesirable genetic traits, such as resistance to toxin, can be inhibited or reversed by introducing sexually compatible individuals substantially homozygous for the sensitive allele, such as the wild type, into the target population.

31 Claims, 9 Drawing Sheets

OTHER PUBLICATIONS

Arribas et al. (1986) "The ubiquitin genes in *D. melanogaster*: transcription and polymorphism" Biochimica et Biophysica Acta 868:119-127.

Atkinson et al. (2000) "*Hermes* and Other *hAT* Elements as Gene Vectors in Insects," *Insect Transgenesis: Methods and Applications*, Hadler et al. eds., Boca Raton CRC Press, pp. 219-235.

Bieschke et al. (Jun. 1998) "Doxycycline-Induced Transgene Expression During *Drosophila* Development and Aging," Mol. Gen Genet. 258(6):571-579.

Blitvich et al. (2002) "Developmental- and tissue-specific expression of an inhibitor of apoptosis protein 1 homologue from *Aedes triseriatus* mosquitoes" Insect Molecular Biology 11(5):431-442.

Cabera et al. (2002) "Expression Pattern of Gal4 Enhancer Trap Insertions Into the *bric à brac* Locus Generated by P Element Replacement," Genesis 34:62-65.

Chen et al. (1996) "Apoptotic Activity of REAPER Is Distict from Signaling by the Tumor Necrosis Factor Receptor 1 Death Domain" The Journal of Biological Chemistry 271(42):25735-25737.

Chen et al. (2000) "The Use of Modified Tetracycline Regulatory Expression System with Reduced Basal Level to Develop and In Vivo Biopesticide Expression System," Food Sci Agricult. Chem. 2(4):220-225.

Elick et al. (1997) "Analysis of the Cis-Acting DNA Elements Required for *piggyback* Transposable Element Excision," Mol. Gen. Genet. 255:605-610.

Ernst, U. (1991) "Regulation of Sexual Differentiation in *Drosophila*: Alternative Splicing of the *Transformer* Primary Transcript Requires Masking of the Non-Specific Acceptor Site in Females," Inaugural Dissertation, Aus Frankfurt / Main, BRD (Abstract Only).

Ernst, U. (1991) "Regulation of Sexual Differentiation in *Drosophila*: Alternative Splicing of the *Transformer* Primary Transcript Requires Masking of the Non-Specific Acceptor Site in Females," Inaugural Dissertation, Aus Frankfurt / Main, BRD.

Funaguma et al. (2005) "The Bmdsx transgene including trimmed introns is sex-specifically spliced in tissues of the silkworm, *Bombyx mori*", Journal of Insect Science (online), 5(17):1-6.

Fussenegger et al. (1997) "Autoregulated Multicistronic Expression Vectors Provide One-Step Cloning of Regulated Product Gene Expression in Mammalian Cells" Biotechnol. Prog. 13:733-740.

Gloor et al. (1991) "Targeted Gene Replacement in *Drosophila* Via P Element-Induced Gap Repair," Science 253:1110-1117.

Gong et al. (2005) "A dominant lethal genetic system for autocidal control of the Mediterranean fruitfly", Nature Biotechnology 23(4):453-456.

Gonzy-Treboul et al. (1995) "Enhancer-Trap Targeting at the Broad-Complex Locus of *Drosophila melanogaster*," Genes Dev. 9:1137-1148.

Gossen and Bujard (2001) "Tetracyclines in the control of gene expression in eukaryotes" Tetracyclines in Biology, Chemistry and Medicine, pp. 139-157.

Handler et al. (2001) "A Current Prospective on Insect Gene Transformation," Insect Biochem. Mol. Biol. 31(2):111-128.

Handler, A. (2002) "Use of *piggyback* Transposon for Germ-Line Transformation of Insects," Insect Biochem. Mol. Biol. 32:1211-1220.

Heslip et al. (1994) "Targeted Transposition at the *vestigial* Locus of *Drosophila melanogaster*," Genetics 138:1127-1135.

Hofmann et al. (1996) "Rapid Retroviral Delivery of Tetracycline-Inducible Genes in a Single Autoregulatory Cassette," Proc. Nat. Acad. Sci. USA 93:5185-5190.

Hondred et al. (1999) "Use of Ubiquitin Fusions to Augment Protein Expression in Transgenic Plants" Plant Physiology 119:713-723.

Horn et al. (2000) "Highly sensitive, fluorescent transformation marker for *Drosophila* transgenesis" Dev Genes Evol 210:623-629.

Horn et al. (2002) "Fluorescent Transformation Markers for Insect Transgenesis," Insect Biochem. Mol. Biol. 32:1221-1235.

Horn et al. (2003) "*piggyBac*-Based Insertional Metagenesis and Enhancer Detection as a Tool for Functional Insect Genomics," Genetics 163(2):647-661.

Johnson-Schlitz et al. (1993) "P-Element-Induced Interallelic Gene Conversion of Insertions and Deletions in *Drosophila melanogaster*," Mol Cell Biol. 13:7006-7018.

Lankenau et al. (1996) "Comparison of Targeted-Gene Replacement Frequencies in *Drosophila melanogaster* at the *Forked* and *White* Loci," Mol. Cell Biol. 16:3535-3544.

Louis et al. (2003) "A Theoretical Model for the Regulation of *Sex-Lethal*, a Gene That Controls Sex Determination and Dosage Compensation in *Drosophila melanogaster*," Genetics 165:1355-1384.

Loukeris et al. (1995) "Introduction of the transposable element *Minos* into the germ line of *Drosophila melanogaster*" Proc. Natl. Acad. Sci. USA 92:9485-9489.

Munoz et al. (2004) "The AeAct-4 gene is expressed in the developing flight muscles of female *Aedes aegypti*", Insect Molecular Biology 13(5):563-568.

Pane et al. (2002) "The *transformer* gene in *Ceratitis capitata* provides a genetic basis for selecting and remembering the sexual fate" Development 129:3715-3725.

*piggyBac* website, http://piggybac.bio.nd.edu/, Mar. 21, 2006, 5 pp.

Rong et al. (2000) "Gene Targeting by Homologous Recombination in *Drosophila*," Science 288:2013-2018.

Rong et al. (2001) "A Targeted Gene Knockout in *Drosophila*," Genetics 157:1307-1312.

Russ et al. (1996) "Self-Deleting Retrovirus Vectors for Gene Therapy," J. Virol. 70:4927-4932.

Saccone et al. (2000) "Sex Determination in Medfly: A Molecular Approach," In; *Area-Wide Control of Fruit Flies and Other Pest Insects*, Tan, K.H. ed., Penerbit USM, Penag, pp. 491-496.

Saccone et al. (2002) "Sex determination in flies, fruitflies and butterflies" Genetica 116:15-23.

Scali et al. (2005) "Identification of sex-specific transcripts of the *Anopheles gambiae* doublesex gene", Journal of Experimental Biology 208(19):3701-3709.

Sepp et al. (1999) "Conversion of *lacZ* Enhanced Trap Lines to *GAL 4* Lines Using Targeted Transposition in *Drosophila melanogaster*," Genetics 151:1093-1101.

Shockett et al. (1995) "A Modified Tetracycline-Regulated System Provides Autoregulatory, Inducible Gene Expression in Cultured Cells and Transgenic Mice," Proc. Nat. Acad. Sci. USA 92:6522-6526.

Stebbins et al. (2001) "Tetracycline-Inducible Systems for *Drosophila*," Proc. Nat. Acad. Sci. USA 98:10775-10780.

Stebbins et al. (2001) "Adaptable Doxycycline-Regulated Gene Expression Systems for *Drosophila*," Gene 270:103-111.

Steiner et al. (1995) "Homologous Recombination as the Main Mechanism for DNA Integration and Cause of Rearrangements in the Filamentous Ascomycete *Ashbya gossypii*," Genetics 140:973-987.

Wobus et al. (1990) "A New Transposable Element in *Chironomus thummi*," Mol. General Genet. 222:311-316.

Wu et al. (2000) "Expression of Highly Controllable Genes in Insect Cells Using a Modified Tetracycline-Regulated Gene Expression System," J. Biotechnol. 80(1):75-83.

Examination Report for European patent application serial No. 04743590.4, dated Nov. 14, 2008, 4 pp.

Search Report Corresponding to Great Britain Patent Application No. GB 0317656.7, Date of Search Nov. 25, 2003.

Search Report Corresponding to Great Britain Patent Application No. GB 0621234.4, Date of Search Feb. 21, 2007.

Search Report Corresponding to International Application No. PCT/GB2004/003263, Mailed May 11, 2004.

Prosecution history for related U.S. Appl. No. 10/148,041, filed Sep. 26, 2002, 64 pp., last entry (Office Action) dated Oct. 10, 2006.

Prosecution history for related U.S. Appl. No. 10/562,843, filed May 15, 2006, 63 pp., last entry (Amendment) dated Nov. 30, 2010.

Prosecution history for related U.S. Appl. No. 10/566,448, filed Jan. 27, 2006, 142 pp., last entry (Amendment) dated Oct. 27, 2010.

Prosecution history for related U.S. Appl. No. 11/352,177, filed Feb. 10, 2006, 129 pp., last entry (Supplemental Amendment) dated Oct. 21, 2010.

Prosecution history for related U.S. Appl. No. 11/733,737, filed Apr. 10, 2007, 175 pp., last entry (Amendment) dated Dec. 6, 2010.

Prosecution history for related U.S. Appl. No. 12/278,849, filed Mar. 6, 2009, 32 pp., last entry (Office Action) dated Dec. 1, 2010.

Office Action, dated Feb. 16, 2011, in U.S. Appl. No. 10/562,843 (International filing date, Jul. 1, 2004).

Office Action, dated Feb. 2, 2011, in U.S. Appl. No. 10/566,448 (International filing date, Jul. 28, 2004).

Office Action, dated Mar. 16, 2011, in U.S. Appl. No. 11/352,177 (International filing date, Feb. 12, 2007).

* cited by examiner

Simple life cycle used in the basic model of *Bt* selection

One generation

Figure 2
Genotypes in the RIDL-release model
Total of 7 male (1 engineered release type, 3 wild-types and 3 F2 types) and 3 female (all wild-types) genotypes
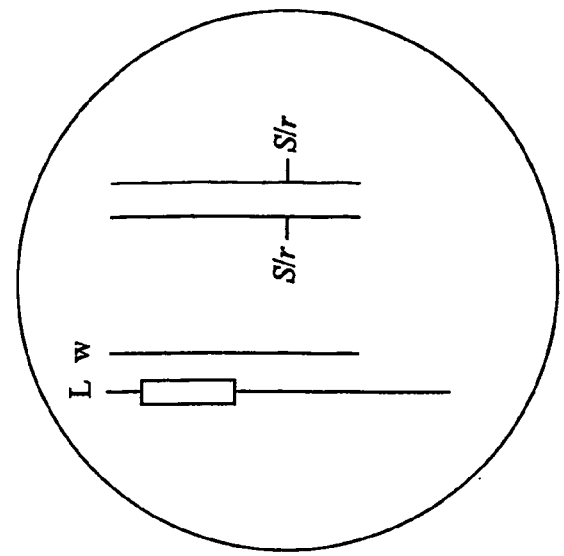
Male (1) engineered genotype for release
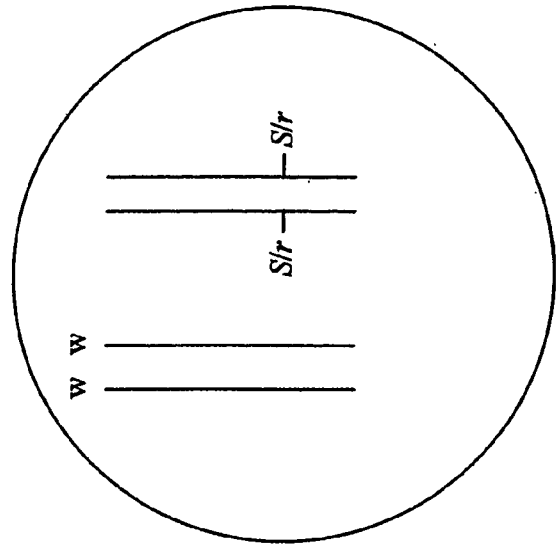
Male (3) and Female (3) "wild-types"
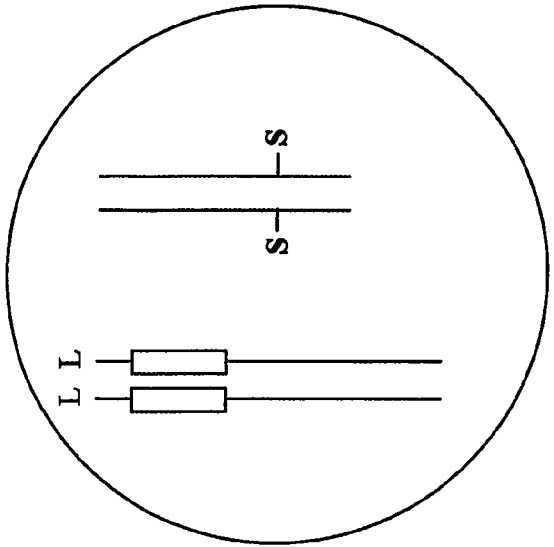
Male (3) F2s

Figure 5a and b

Figure 8a and b
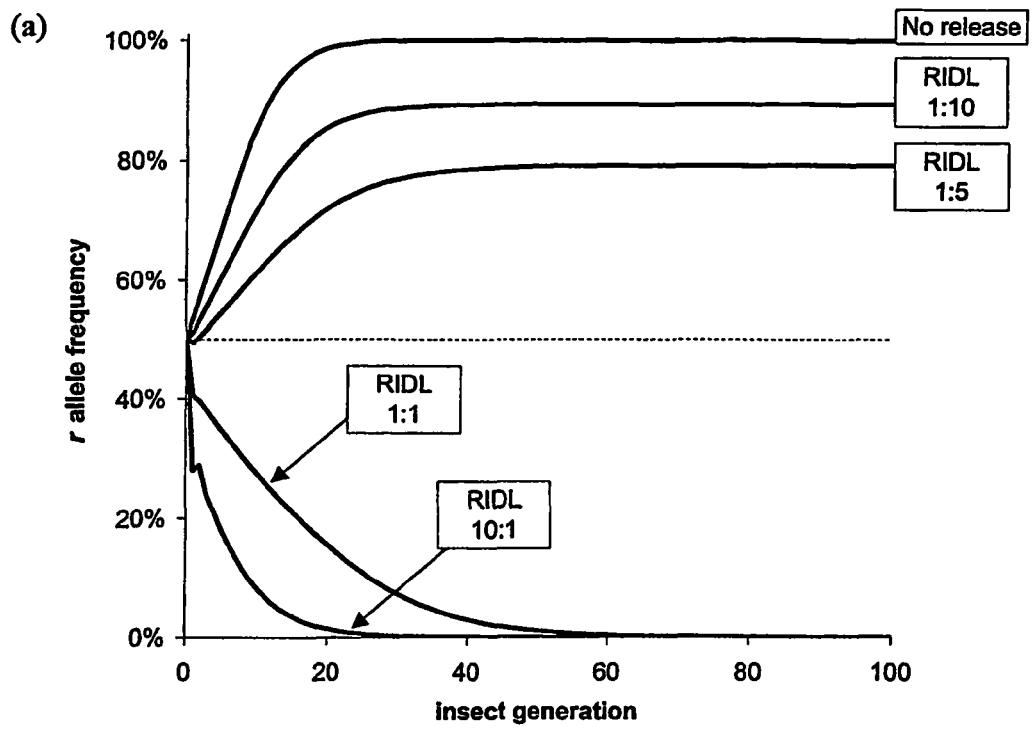
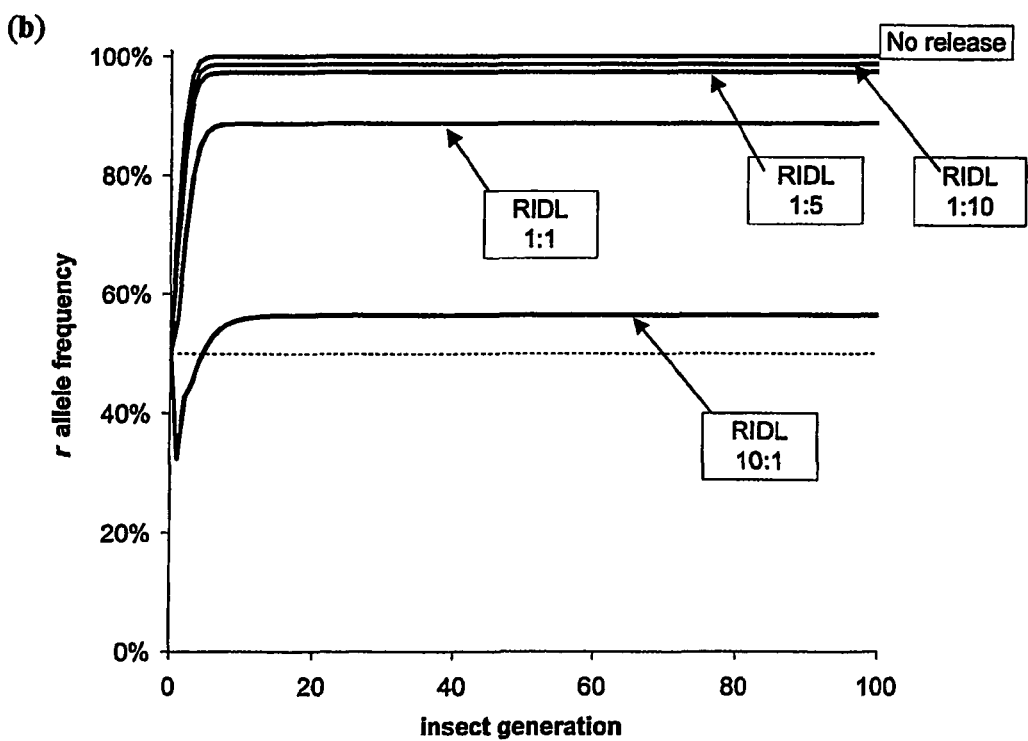

DILUTION OF GENETIC TRAITS

CROSS-REFERENCE TO RELATED APPLICATIONS

This application is a national stage application under 35 U.S.C. §371 of PCT/GB2004/002021, filed May 12, 2004, which takes priority from GB patent application no. 0310880.0, filed May 12, 2003, both of which are incorporated by reference in their entirety herein.

The present invention relates to breeding strategies for reducing the frequency of, or eliminating, genetic traits, such as pesticide resistance, in a target population.

Ways of controlling pests, and especially those which attack important harvests or which are capable of spreading disease, are continually being sought. With each new strategy that is found, for eliminating or neutralising a pest, comes the concern that the pest in question will develop resistance, or become immune, to the strategy.

For example, the Cry1Ac protein from *Bacillus thuringiensis* can successfully be expressed in many important crops, and is effective as a pesticide, both when used as a spray or when expressed by the plants themselves. However, instances of resistance to Bt toxin have already been noticed amongst the diamondback moth population, for example. As resistance spreads, alternative strategies for controlling pest populations will have to be found.

Resistance genes generally confer a level of selective disadvantage. If this were not the case, then the genes would normally be present at substantial levels in the population already, and would spread exceedingly rapidly, once use of the toxin became commonplace. Such genes may exert their effect by blocking a particular pathway, or by preventing a particular substance from crossing the cell membrane, for example.

Even at the simplest level, where only one locus is associated with resistance, most resistance genes show some degree of partial or co-dominance. Thus, pests which are heterozygous for the resistance gene still show some resistance to the toxin, especially at low levels of toxin. This is not always the case, and some Bt resistance, for example, appears to be purely recessive, i.e. if the insect is not homozygous for resistance, then there is no resistance.

Accordingly, the spread of resistance is often difficult to spot, as insects only heterozygous for the resistance gene will show only some selective advantage in areas where the pesticide is used and, by the time that homozygous insects start to be commonplace, a large proportion of the population will contain at least one resistant gene, so that the effect is effectively for a resistant population to appear "out of nowhere".

Various strategies are employed for minimising pesticide resistance. Commonly used strategies include: endeavouring to minimise use, thereby reducing the selective pressure for development of resistance; the use of different toxins in combination, as well as developing and using new pesticides, so as not to encourage resistance to develop against any one particular pesticide; the use of toxins at high concentration formulation to increase the effect on heterozygotes or weakly resistant individuals; and the use of pesticides within an integrated pest management framework.

Other methods for reducing the pest population size, such as using the conventional Sterile Insect Technique (SIT), can also have the effect of increasing the level of inbreeding, which can increase the rate at which homozygous resistant genotypes appear. A particular problem associated with this technique lies in the fitness, or competitiveness, of the sterile insects, which can be as low as a tenth that of the wild type.

Given that the quantity of the next generation eliminated by this technique can be only as high as 50%, for 100% release by numerical comparison with the wild population, it is necessary to release numbers in excess of several times the indigenous population in order to have a significant effect.

More recently, especially with the use of Bt crops, the "high dose/refuge strategy" has started to be employed. In this strategy, a "refuge" of non-transformed plants is provided, in addition to the Bt plants. The purpose of this is to encourage the proliferation of sensitive, or wild-type, insects in the refuge areas, so that the sensitive genes will continue to be encouraged, and spread into the resistant insects, to dilute the onset of resistance. The "high dose" relates to the plants, which provide a sufficiently high dose of the Bt toxin to kill off any insects which are only heterozygous for resistance, thereby forcing the resistance to become a recessive trait, i.e. only insects homozygous for the resistance gene will survive. Sensitive genes carried by the insects breeding in the refuges then serve to generate heterozygotes which cannot survive the high dose plants. The use of the high dose/refuge strategy does not preclude the complementary use of pesticides, or other pest control methods.

Population models show that this strategy should greatly restrict the spread of resistance, but will generally only be effective to slow it down. Even with refuge areas as high as 50%, the complete spread of resistance may only delayed by as little as 10 years, after which substantial or complete resistance can be expected to have rendered the toxin useless.

In addition, end user compliance is likely to be exceedingly difficult to enforce, as it is not in the immediate commercial interests of a farmer to use no pest control strategy, or a sub-optimal one, on a significant percentage of his crop, hence potentially allowing 20% or more of his crop to be destroyed by pests, simply in order to continue to be able to use that same toxin in 10 years time. Although this effect can be ameliorated by the use of other pesticides on the refuges, there will remain a significant temptation not to plant refugia.

There is also the possibility of employing a "non-high dose/refuge" strategy, such as has recently been proposed in relation to an anti-corn root worm product, where some experts considered that the appropriate refuge size should be 50%, as the level of Bt toxin expressed only kills about half of the root worm larvae. Any resistance could, therefore, be expected to spread rapidly. However, a refuge of 50% is unlikely to be commercially acceptable in many quarters, which has lead to calls for a 20% refuge that may be less effective at halting the spread of resistance.

WO 01/39599 discloses a method for controlling the population of a pest, such as an insect, by the release of insects carrying dominant lethal genes. The dominant lethal gene is suppressible under controlled conditions but, on release, the lethal phenotype is expressed. In order for this RIDL release to continue to be effective, the dominant lethal is generally sex specific, and is generally chosen to kill all female progeny. With time, however, resistance or tolerance can arise to any specific genes used in the RIDL technique.

At present, once resistance begins to appear, the best that can be done is to slow down the spread of resistance, with the only guaranteed way to stop resistance spreading any further being the cessation of use of the toxin, or pesticide. There is a clear need for further methods for slowing the spread of resistance and, particularly, for preventing or even reducing or eliminating established resistance.

Surprisingly, it has now been found, where a pest reproduces sexually, and especially where carriers of resistance genes have lesser fitness than the wild type under conditions not selective for resistance, then simple introduction of the wild type into a population is sufficient to reduce or prevent the spread of resistance and, at high enough levels, is even capable of eliminating established resistance.

Thus, in a first aspect, the present invention provides a method for the inhibition or reversal of the spread of a non wild type genetic trait in a non human population capable of sexual reproduction, the trait conferring a reduced level of fitness of the individuals carrying that trait in either the heterozygous or homozygous form, the method comprising introducing sexually compatible individuals substantially homozygous for the wild type counterpart of the trait into the target population.

This method is distinct from the simple use of refuges, or refugia, in that the individuals released into the target population are guaranteed to be free, or substantially free, of resistance. By contrast, with the use of refugia, there is no selection against the resistance phenotype other than the relative fitness of the genotype it carries. Thus, typically, greater and greater levels of insects carrying at least one copy of the resistance gene will form the population characterising the refugia so that, eventually, resistance will become the norm.

By contrast, the method of the present invention guarantees a pure, or substantially pure, influx of individuals homozygous for the sensitive gene, thereby diluting the resistance gene pool. With continued use of the method, the simple fact that individuals carrying resistance genes have reduced levels of fitness in the absence of the selective agent, combined with simple dilution of the resistance allele, will restrict, prevent, or even reverse the spread of resistance.

Individuals heterozygous for the resistance gene(s) generally have much lower fitness on the toxin than homozygotes which, combined with the dilution effect that greatly reduces the number of resistant homozygotes, tends to reduce the overall fitness of the resistance allele. Without introduction of further wild type in accordance with the invention, the frequency of homozygotes increases dramatically, beyond a certain point. However, the introduced wild type dilutes both heterozygotes and homozygotes, largely preventing escalation of homozygote numbers, with the less fit heterozygotes being at a disadvantage both in the presence of toxin (against homozygotes) and in its absence (against wild type).

This effect results not only from reducing the allele frequency, but also by preventing the population reaching Hardy-Weinberg equilibrium. With continued use of the method, the simple fact that the released individuals do not, or predominantly do not, carry resistance alleles, and so tend to dilute the resistance alleles within the population, and particularly the relative frequency with which homozygous resistant individuals arise, will restrict, prevent, or even reverse the spread of resistance.

Suitable populations will generally be wild populations, such as mosquitoes, for example, but may be any suitable population in which it is desired to control the spread of a non wild type trait, or trait where an increased fitness alternative can be used to control the trait. Cultivated plant crops may develop abnormal growth, for example, and release of appropriate pollen may be used to eliminate or reduce further incidence.

By "sexually compatible" is meant that the individuals introduced into the population are capable of sexual reproduction with members of the target population. The individuals are preferably of the same species, but this is not essential, provided that fertile or partially fertile offspring are possible. Where the introduced individuals are essentially wild type, then there is no effective restriction on reproduction. Other individuals, such as are described below, may carry traits that affect future generations in some way, preferably rendering them unfit.

As used herein, "unfit" and associated terms can refer to simple lethality, or can otherwise refer to characteristics which, while not killing the insect, render it substantially unfit for reproduction, such as blindness, flightlessness, and sterility, including sexual transformation, or any other property or characteristic which renders them uncompetitive or less than fully vigorous under at least some circumstances.

The term "fitness", as used herein, generally relates to the numbers of viable progeny able to be produced in the next generation compared to the wild type, which is deemed to have a relative fitness of 1, in the absence of any selective agent. Considerations of fitness can be complicated, for example, where a dominant lethal gene is inherited, killing some of a generation and not others. Those that live may be 100% fit, but overall, or average, fitness maybe considered as being 50%, if half of the next generation is killed as a result of inheriting the lethal gene. Some heterozygotes, for example, may have fitness levels as high as 0.99 and occasionally as high as 1, whereas the homozygote resistant types may only have a fitness level of 0.5, or lower, depending on the nature of the resistance gene. Traits having fitness levels of less than 1 are particularly preferred targets for the present invention.

The wild type counterpart will generally be the, or a, gene found in the wild which has no, or not as great, a fitness penalty in the absence of the toxin against which it is desired to reduce, eliminate or prevent the spread of resistance.

In an alternative aspect, the present invention provides a method for the inhibition or reversal of the spread of a genetic trait in a non human population capable of sexual reproduction, the method comprising introducing sexually compatible individuals substantially homozygous for a counterpart of the trait into the target population, the trait conferring a reduced level of fitness on individuals carrying that trait in either the heterozygous or homozygous form, or both, compared to individuals homozygous for the counterpart.

The heterozygotes may suffer no relative fitness penalty, compared to the wild type, or individuals homozygous for an allele with a higher fitness, but will generally have reduced fitness compared with individuals homozygous for resistance, when in the presence of toxin. This reduced fitness in the presence of toxin will reduce the gene pool for resistance, the pool being topped up by the wild type, or sensitive, genes in the released individuals, thereby reducing or preventing the spread of resistance. Resistance can even be eliminated by this method.

The counterpart need not necessarily be the corresponding wild type of the trait to be inhibited or reversed, provided that it is associated with greater levels of fitness under conditions not selective for the trait. Preferred counterparts restore the wild type condition to members of the population, but others may encode a non wild type trait to replace the trait with another, such as a marker, or even a conditional lethal, or may replace a wild type trait with another trait.

The counterpart may be one or more homologues of the gene or genes for the trait, or may be a replacement therefor, including an inactive gene or deletion, where this confers a higher fitness and eliminates the trait when the individual is homozygous therefor. The counterpart should preferably be located at the same place on the chromosome as that of the gene for the undesirable trait, although this is not essential, such as where resistance arises through a lack of expression, or where the gene conferring the sensitive phenotype restores, or counteracts the resistant phenotype, for example.

It will be appreciated that the target population may be vegetable, or non human animal and, that while the target population referred to herein will generally be referred to as "insects", it will be understood that the use of this and related terms equally applies to other types of population suitable for targeting by the method of the present invention. Any suitable traits may be targeted by the method of the present invention and, while pesticide resistance is a significant target, and one that is particularly preferred, tolerance or susceptibility to environmental conditions such as chemicals, temperature etc, or to biological control agents such as predators, viruses, other parasites and parasitoids, and other traits, such as abnormalities in growth, breeding or appearance, for example, may also be targeted.

A trait which confers no selective disadvantage cannot actually be eliminated by the method of the present invention, although it may be diluted, but spread will always be beneficially slowed relative to existing strategies. The method may also be slow to yield results in populations which have significant time delays between generations. It is preferred, therefore, for populations targeted by the method of the present invention to have at least an annual breeding cycle, and preferably to have two or more breeding cycles in a year.

It is a particular advantage of the present invention that any form of resistance can be mitigated, including resistance to the method of the present invention, and multiple resistances, even where a resistant condition has not been recognised. The effect is particularly notable when the homozygote and, especially the heterozygote, suffers a fitness penalty, in the absence of the compound to which resistance is conferred, compared to the wild type.

The methods of the invention have the particular advantage that multiple resistances can be overcome at once, even where any particular resistance is unknown or not recognised, as, provided the wild type gene is present, then it will dilute any resistance gene present. Any resistance may be targeted, even resistance to the methods of the invention.

Likewise, use of the methods of the invention will generally also result in the suppression of the spread of any new mutation that may occur, where such mutation has reduced fitness. Mutations without a fitness penalty will still be diluted, however.

The present invention is as applicable to complex resistance, involving two or more genes, as to simple resistance involving only one locus. It is only necessary for the individuals released into the target population to be homozygous for one wild type, or reduced fitness penalty, gene. However, it is preferred that the released individuals are homozygous for the wild type, or reduced fitness penalty, counterparts of 2, 3, or more, and preferably all, of any complex resistance, or trait, that may be observed.

It will be appreciated that the terms "resistance" and "trait" are used interchangeably herein, and that any reference to the term "resistance", or equivalent language, incorporates reference to any suitable trait targetable by the present invention, unless otherwise apparent.

Suitable toxins against which resistance might be raised include both naturally occurring and manufactured pesticides and control agents, such as growth control or suppressing agents, and include naturally expressed toxins, such as Bt toxin, whether the toxin is heterologous or homologous to the crop. Any form of genetically encoded resistance is targetable by the present invention.

The method of the present invention may be used in combination with any other method used for controlling or affecting a population. For example, it is advantageous to employ refugia with the methods of the invention, in order to allow wild type, or "sensitive", genes to increase in frequency. The use of refugia is particularly preferred where the substance for which resistance is sought to be reduced, prevented or eliminated is present in high doses and there is no other natural food source for the pest and/or in circumstances where the resistance allele is at a significant fitness disadvantage relative to wild type in such a refuge.

In general, only small refugia will be necessary for optimal conditions, and it will frequently be sufficient to use no deliberately planted or provided refugia at all, such as where alternative food sources are available, such as domestic plantings, or where there is a significant influx of non-resistant individuals.

Refugia, where used, may be of any appropriate size, as determined by those skilled in the art. As a guide, suitable sizes, expressed as a percentage of total planting area, are between 0.1% and 50%, more preferably between 1 and 20%, with a size of about 5% being a preferred size.

The size of any refugia will also be dependent on location and cluster size. For example, it may be sufficient simply to mix 5% non-Bt seeds with a supply of Bt seeds, where the method is to combat the spread of Bt resistance. Where a refuge is distinct from the main planting, then a size of 10%, or greater, may be desirable.

Individuals for release into target populations are preferably entirely homozygous for the wild type counterpart of the resistance gene, but it will be appreciated that there is some possibility that a low level of the resistance gene may be present in the cultivated individuals. This is generally undesirable, and can be substantially completely eliminated by the appropriate choice of breeding stock and breeding conditions which should, preferably, entail the complete absence of the toxin appropriate to the resistance gene.

Methods for monitoring the cultivated stocks may also be used to ensure that the resistance gene is kept at minimal, or preferably zero levels.

In general, it is undesirable to release large quantities of wild type pests, even if the end result is to eliminate resistance to a particular pesticide. Large quantities of mosquitoes, for example, or crop devouring pests will often not be seen as being advantageous.

Surprisingly, it has been established that release of individuals, or insects, with dominant lethal genes, but which carry the wild type counterpart of the present invention for the target trait, not only controls, or tends to control, the population, but prevents, reduces or reverses the incidence of resistance in the population.

Thus, in a further aspect, there is provided a method as described above, wherein the individuals released into the target population carry a dominant lethal trait, or trait which results in reduced fitness in at least some individuals in at least one subsequent generation. 100% lethality in the $F_1$ generation is not preferred.

It is particularly preferred that the sensitive, or wild type, gene not be appreciably linked to the dominant lethal gene. Preferable, the sensitive, or wild type, gene is on a different chromosome from the dominant lethal gene, or is substantially removed from the dominant lethal, if on the same chromosome. Thus, as the gene is carried through the generations, the resistance trait will become associated with the dominant lethal in up to half of the individuals carrying the dominant lethal, so that copies of the gene will be eliminated in subsequent generations where the lethal kills the progeny, such as all of the female progeny in the case of a 100% effective female specific dominant lethal.

In this aspect of the invention, it has been found that the effective control is increased, so that release of individuals carrying a dominant lethal gene and carrying a suitable wild type gene provides a synergistic method for controlling a pest population.

It is preferred that the lethal trait not confer 100% death rate on the immediate succeeding generation prior to any opportunity that that generation may have to sexually reproduce. It is acceptable for mortality rates to be high, possibly as much as 99%, for example, but if the wild type counterpart gene is not passed on to succeeding generations, then there will be no impact on the spread of resistance, other than through reduction in the population.

It will be appreciated, therefore, that SIT is not generally preferred as a vehicle for the wild type counterpart genes, as SIT generally results in no introgression of any genotype. However, an SIT technique wherein the individuals merely have a compromised, rather than totally eliminated, ability to reproduce may be employed.

Another suitable method to combine with the method of the present invention is that of $F_1$ sterility, which is of particular use with the Lepidopterans, wherein a low dose of radiation is sufficient to sterilise females but not males. However, with the correct selection of radiation dose, the female offspring of the irradiated males will also be sterile.

In another technique, cultivated individuals raised under control conditions may be homozygous for a lethal gene and an appropriate suppressor therefor. It is generally preferred that these not be linked so that, whilst the $F_1$ generation will all survive, the $F_2$ generation will suffer 25% mortality, assuming partnering with only wild types.

More preferably, the present invention envisages the use of suppressible, or conditional, dominant lethal genes in combination with the methods of the invention.

Suitable dominant lethals are generally controlled by environmental conditions, such as temperature, diurnal rhythm or dietary components, such as tetracycline. Suitable systems which may be adapted for use in the present invention include those described by Heinrich et al. (PNAS (2000), 97, vol. 15, 8229-8232) and Thomas et al. (Science (2000), 287, 2474-2476). Pre-release construction or activation of a lethal, e.g. a female-specific lethal, by use of site-specific recombinases, such as F1p/FRT or cre/lox, is also envisaged. Thus, in vivo construction or activation of a lethal by use of site-specific recombinases or other DNA-modifying agents is also envisaged.

In general, it is preferred that the dominant lethal gene be selective, and it is generally preferred that the selectivity be for the female, in order to reduce the number of progeny. However, the present invention also envisages male specific dominant lethals.

In certain circumstances, it will be appreciated that it may be desirable to label either the wild type or the dominant lethal gene, in order to follow progress through the target population. Suitable labels are well known, such as dyes or phenotypic markers. It will be appreciated that such markers should be as closely linked as possible to the gene, in order to ensure that they are, indeed, marking the passage of the gene. As such, it will be appreciated that the marker should preferably be immediately adjacent the selected gene.

Individuals suitable for release into target populations may be bred by any recognised means. Where the individuals carry a dominant lethal, then this should generally be suppressed, as far as possible, during preparation of a release population, in order to maximise yield. In some circumstances, it may be appropriate to remove any suppression before release to allow the final generation to be affected, such as in the case of female specific lethals, so that only male "carriers" are released into the target population. This is particularly appropriate where the female is a pest in itself such as with mosquitoes and medfly, for example.

Suitable populations that may be targeted include those of the following species:
Australian sheep blowfly (*Lucilia cuprina*)
New world screwworm (*Cochliomyia hominivorax*)
Old World Screwworm (*Chrysomya bezziana*)
Tsetse fly (*Glossina* spp)
Stable Fly (*Stomoxys calcitrans*)
Face Fly (*Musca autumnalis*)
Other *Musca* species (e.g. *Musca domestica*)
Horn Fly (*Haematoba irritans*)
Asian tiger mosquito (*Aedes albopictus*)
yellow fever mosquito (*Aedes aegypti*)
malaria mosquitoes, e.g. (*Anopheles gambiae, Anopheles stephensi, Anopheles funestus, Anopheles arabiensis, Anopheles dirus, Anopheles albimanus*)
Other mosquito vectors of disease, e.g. (*Culex pipiens, Culex quinquefasciatus*)
Japanese beetle (*Popilla japonica*)
White-flinged beetle (*Graphognatus* spp.)
Boll weevil (*Anthonomous grandis*)
Corn Rootworms: Western (*Diabrotica virgifera virgifera*), Northern (*Diabrotica barberi*), Southern (*Diabrotica undecimpunctata howardi*) and Mexican (*D. virgifera zeae*)
Red Palm Weevil (*Rhynchophorus ferrugineus*)
Sweet potato Weevils (*Cylas formicarius, eucepes postfasciatus*)
Colorado beetle (*Leptinotarsa decemlineata*)
Pine Shoot Beetle (*Tomicus piniperda*)
Mahogany Shoot Borer (*Hypsipyla robusta*)
Flour Beetle (*Tribolium confusum*)
Pea Weevil (*Bruchus pisorum*)
Grain borers (*Prostefanus truncatus, Rhyzopertha dominica*)
Flat grain beetle (*Cryptolestes ferrugineus*)
Granary & Rice Weevils (*Cytophilus* spp.)
Citrus blackfly (*Aleurocanthus woglumi*)
Oriental fruit fly (*Dacus dorsalis*)
Olive fruit fly (*Dacus oleae*)
tropical fruit fly (*Dacus cucurbitae, Dacus zonatus*)
Mediterranean fruit fly (*Ceratitis capitata*)
Natal fruit fly (*Ceratitis rosa*)
Cherry fruit fly (*Rhagoletis cerasi*)
Queensland fruit fly (*Bactrocera tryoni*)
Caribbean fruit fly (*Anastrepha suspensa*)
Carambola Fruit Fly (*Bactrocera carambolae*)
Mexican Fruit Fly (*Anastrepha ludens*)
Onion Fly (*Delia antiqua*)
Mushroom flies (*Lycoriella mali, Lycoriella auripila* & *Megaselia* spp.)
Other fruit flies (*Tephritidae*)
Gypsy moth (*Lymantria dispar*)
Codling moth (*Cydia pomonella*)
Brown tail moth (*Euproctis chrysorrhoea*)
rice stem borer (*Tryporyza incertulas*)
Pink Bollworm (*Pectinophora gossypiella*)
Navel Orangeworm (*Amyelois transitella*)
Peach twig worm (*Anarsia lineatella*)
Painted Apple Moth (*Teia anartoides*)
Corn Earworm (*Helicoverpa armigera, Helicoverpa zea*)
Tobacco Budworm (*Heliothis virescens*—and other *Heliothines*)
Tobacco Hornworm (*Maduca sexta*)
Potato Tuber Moth (*Phthorimaea operclella*)
Date Moth (*Ectomyelois ceratoniae*)
Oriental Fruit Moth (*Grapholita molesta*)

Diamondback moth (*Plutella xylostella*)
Indian Meal Moth (*Plodia interpunctella*)
Greenhouse Whiteflies (e.g. *Bemisia tabaci, Trialezodes vaporarium*)
Cattle Fever tick (*Boophilus microplus*) and other ticks of veterinary importance and
Psocids (*Liposcelis* spp.).

Suitable quantities for release are generally calculated in accordance with the expected size of population into which they are to be released. With methods such as SIT, these sizes are typically between 5 and >100 times the size of the target population. Using the method of the present invention, with a sex specific dominant lethal and 50% refugia, it is only necessary to release an amount of individuals corresponding to 0.3 (³⁄₁₀ or 30%), the size of the target population to completely reverse the spread of some types of resistance. These figures depend on many factors, including relative fitnesses and refugia sizes, so that release sizes will necessarily vary, and have differing efficacies, according to such parameters. Releases of 10% and lower also have a significant effect on the spread of many types of resistance.

Size estimations will often be approximate, as population densities may be only approximately known, and it may not be apparent how far the released individuals may penetrate into the target population.

Accordingly, where there is no imminent threat of resistance developing, for example, releases of as low as 0.1%, for example, may be sufficient to prevent resistance developing, although it is generally preferred to release between 1 and 10% for control purposes. Where there is a threat, or where the release is coupled with other control means, such as RIDL, then releases of between 10 and 10,000% are preferred, with 30 to 5,000% being more preferred, especially 50 to 1000%. Such releases can be repeated as often as necessary, typically once per generation, although other regimens will be apparent to those skilled in the art.

The values used to calculate release numbers depend on various parameters, especially the relative competitiveness (C) of the released individuals and the reproductive rate of the wild population ($R_0$). Neither is easy to measure, but estimates can be obtained, particularly as the program progresses. In general, it is preferred that the release rate is more, and preferably substantially more, than $(R_0-1)/C$. Relative competitiveness might typically be 0.1-0.5, while $R_0$ varies by species, but will generally be in the range 1.5-10. Appropriate minimum release rates may then be from 1-90 (100% to 9000%) for population control, but resistance management will generally be effective at considerably lower rates. Population control will also be effective at lower rates where RIDL is combined with another control method, such as the use of Bt, or other toxin, which will often be the case when using the methods of the invention.

As used herein, $R_0$ is the maximum average reproductive rate under normal conditions, i.e. ignoring density-dependent effects, and will be reduced in the presence of a toxin, for example. If $R_0$ were not greater than 1 under normal conditions, the population would not expand and would be unlikely to be considered a pest.

Where reducing or eliminating resistance is referred to herein, it will be understood that this includes use of the methods of the present invention in circumstances where significant resistance already exists. For example, the frequency of a resistance allele in a population where it has already attained an economically significant level, e.g. 20%-99%, may be reduced by the release of, preferably very large, amounts of sensitive individuals. This may advantageously be in conjunction with reducing, e.g. to zero, the use of the treatment against which the resistance has developed. Use of the invention, especially where the released individuals carry a dominant lethal gene, will always tend to increase the rate at which the resistance allele is eliminated or substantially eliminated, or reduced below an economic threshold, from a population, and can be used to reduce the frequency of the resistance allele under circumstances where, without such releases, it would instead increase in frequency.

The methods of the invention are also suitable to ensure, or encourage, grower compliance, as it is not necessary for the grower to be responsible for the treatment, and those skilled in the art may determine the best policy for protection against resistance developing in any given geographical locale.

It will be appreciated that the present invention extends to methods for the preparation of individuals for release, as well as to the individuals themselves, where novel.

The invention further provides a method for calculating the necessary amount of individuals required for release in order to inhibit, prevent or reverse the spread of a genetic trait, comprising the use of any one or more of the techniques and/or formulae described herein.

BRIEF DESCRIPTION OF THE DRAWINGS

FIG. 2 shows the genotypes in the RIDL-release model;
FIG. 8 illustrates reversing established resistance.

The invention will now be further illustrated with respect to the accompanying, non-limiting Examples, which are for purposes of illustration only.

EXAMPLE 1

A Population Genetics Framework to Examine the Effects of Refugia and RIDL Release on the Management of Bt Resistance in a Pest Population Model Structure and Assumptions We assume that the pest insect population is distributed at random across a fixed crop population, a proportion $\Phi$ of which expresses Bt toxins. The conventional (non-Bt) crop refuge size is therefore $1-\Phi$. Within the insect population, susceptibility to the Bt toxins in the larval stage is assumed to be controlled by a single autosomal locus existing as two alleles; sensitive, S, and resistant, r. Therefore, there are three genotypes in the wild population, SS, Sr and rr.

We further assume that all fitness costs associated with the S and r alleles, in Bt and non-Bt crops, operate prior to adulthood, e.g. during the larval stage. Under the assumption of a random distribution of larvae across Bt and non-Bt crops, the average relative fitness, $\Omega$, of larvae of genotype i is $$\Omega_i = [\omega_i \Phi + \upsilon_i (1-\Phi)], \quad \text{(eq. 1)}$$

where $\omega_i$ is the relative fitness of larvae in the roots of Bt crops, and $\upsilon_i$ is the relative fitness of larvae in non-Bt crops (which is set equal to 1 for the wild-type SS genotype).

Figure 1:
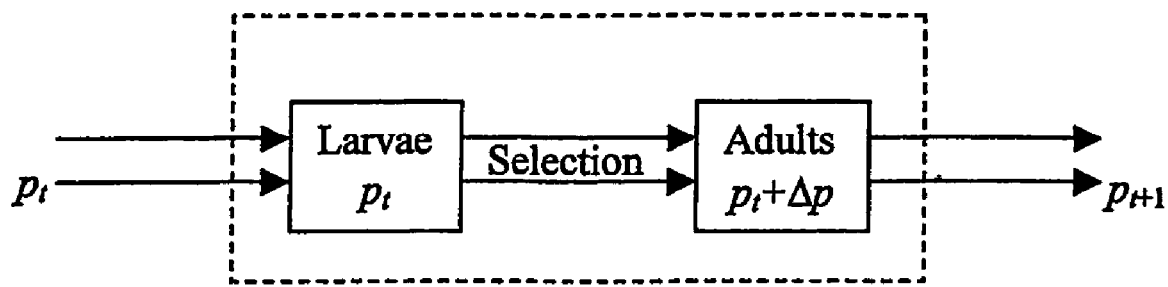
FIG. 1 shows a simple life cycle used in the basic model of Bt selection.

If the frequency of the resistance r allele is p in the adult generation t, then, assuming no mutation, the change in allele frequency in generation t+1, $\Delta p$, is given by $$\Delta p = \frac{p_t^2 \Omega_{rr} + p_t q_t \Omega_{Sr}}{q_t^2 \Omega_{SS} + 2 p_t q_t \Omega_{Sr} + p_t^2 \Omega_{rr}} - p_t, \quad (eq.\ 2)$$

where $q_t = 1 - p_t$. A simple conceptual framework for the model is shown in FIG. 1, below.

Equilibrum Allele Frequency

Setting equation 2 equal to zero and solving which respect top reveals there are three fixed points of resistant allele frequency, $p^*$ at which $\Delta p = 0$. These fixed points are $p^* = 0$, $\rho$ and 1, where $$\rho = \frac{(\upsilon_{Sr} + \omega_{Sr}\Phi - \upsilon_{Sr}\Phi - \omega_{SS}\Phi + \Phi - 1)}{(2\upsilon_{Sr} - 2\upsilon_{Sr}\Phi + 2\omega_{Sr}\Phi + \upsilon_{rr}\Phi - \omega_{rr}\Phi - \omega_{SS}\Phi - \upsilon_{rr} + \Phi - 1)}. \quad (eq.\ 3)$$

The stability of these equilibria is dependent on the relative fitness of the different genotypes in Bt ($\omega_i$) and non-Bt ($\upsilon_i$) crops and the proportion crops expressing Bt (($\Phi$)).

Stable Intermediate Equilibrium

Importantly, $\rho$ only exists as a stable equilibrium lying between 0 and 1, if the proportion of Bt falls between a lower, $\Phi_1$, and upper, $\Phi_2$, critical threshold, provided $\Phi_1 < \Phi_2$.

The lower critical thresholds may be found by setting $\rho$ equal to 0 in equation 3 and solving with respect to $\Phi$ to give $$\Phi_1 = \frac{(1 - \upsilon_{Sr})}{(1 - \upsilon_{Sr} + \omega_{Sr} - \omega_{SS})}. \quad (eq.\ 4)$$

Similarly, the upper critical thresholds may be found by setting $\rho$ equal to 1 in equation 3 and solving with respect to $\Phi$ to give $$\Phi_2 = \frac{(\upsilon_{rr} - \upsilon_{Sr})}{(\upsilon_{rr} - \upsilon_{Sr} + \omega_{Sr} - \omega_{rr})}. \quad (eq.\ 5)$$

Provided $\Phi_1 < \Phi_2$, then if the proportion of Bt crops lies between $\Phi_1$ and $\Phi_2$ the frequency of the r allele will settle at a stable equilibrium $p^* = \rho$, which lies above zero and below 1. However, if the proportion of Bt crops lies below $\Phi_1$, the frequency of the resistant allele will decline to extinction (i.e. $p^* = 0$). Conversely, if the proportion of Bt crops is above $\Phi_2$, the resistant allele will eventually go to fixation (i.e. $p^* = 1$).

Unstable Intermediate Equilibrium

The fixed point $\rho$ is unstable, however, if $\Phi_1 \geq \Phi_2$ and so the resistant allele will eventually either go to extinction or fixation. Under the unstable conditions, the resistant allele will only spread if the frequency p is greater than $\rho$. We can, therefore, derive a third threshold for the proportion of Bt crops, $\Phi_3$, which determines whether the resistant allele will go to fixation or extinction, under the condition that $\Phi_1 \geq \Phi_2$. By setting $p = \rho$ in equation 3 and solving with respect to $\Phi$ we can show that $$\Phi_3 = \frac{(\upsilon_{Sr} - 2p\upsilon_{Sr} + p\upsilon_{rr} + p - 1)}{\upsilon_{Sr} - \omega_{Sr} + \omega_{SS} + p - 2p\upsilon_{Sr} - p\omega_{rr} + p\upsilon_{rr} + 2p\omega_{Sr} - p\omega_{SS} - 1}. \quad (eq.\ 6)$$

So when the equilibrium frequency $\rho$ unstable (i.e. when $\Phi_1 \geq \Phi_2$), the resistant allele will spread to fixation if the proportion of Bt crops is greater than $\Phi_3$. If $\Phi < \Phi_3$, the frequency of resistant allele will decline to extinction. Finally, if $\Phi = \Phi_3$ the frequency will remain constant, although slight perturbations in $\Phi$ above or below the critical threshold $\Phi_3$ will result in fixation or extinction, respectively, of the r allele.

Complete Recessiveness

If $\omega_{Sr} = \omega_{SS}$ (or $\omega_{Sr} = \omega_{SS} = 0$) and $\upsilon_{Sr} = \upsilon_{SS} = 1$, then again fixation determined with respect to $\Phi_3$. In this special case of complete recessiveness in the phenotypes expressed in both Bt and non-Bt crops, then $\Phi_2 = \Phi_3$. We can show this by substituting in equation 5 to give $$\Phi_2 = \frac{1 - \upsilon_{rr}}{(1 - \upsilon_{rr}) + (\omega_{rr} - \omega_{Sr})}. \quad (eq.\ 7)$$

Similarly we can substitute into equation 6 to give $$\Phi_3 = \frac{1 - 2p + p\upsilon_{rr} + p - 1}{1 - 2p + p\upsilon_{rr} + p - 1 + 2p\omega_{SS} - p\omega_{SS} - \omega_{SS} + \omega_{SS} - p\omega_{rr}}. \quad (eq.\ 8)$$

which simplifies to $$\Phi_3 = \frac{1 - \upsilon_{rr}}{[(1 - \upsilon_{rr}) + (\omega_{rr} - \omega_{SS})]}. \quad (eq.\ 9)$$

This can be intuitively interpreted as the difference in fitness between the wild-type and homozygous recessive in non-Bt crops, divided by the magnitude of the sum of fitness differences in both Bt and non-Bt crops.

Complete Dominance

Note, if $\omega_{Sr} = \omega_{rr}$ and $\upsilon_{Sr} = \upsilon_{SS}$ then fixation determined with respect to $\Phi_3$. In the special case of complete dominance in the phenotypes expressed in both Bt and non-Bt crops, then $\Phi_1 = \Phi_3$. Equation 4 cannot be simplified, but as you can see equals the difference in fitness between the wild-type and the resistant genotypes in non-Bt crops, divided by the magnitude of the sum of fitness differences in both Bt and non-Bt crops. By substituting in equation 6 we get $$\Phi_3 = \frac{(\upsilon_{rr} - 2p\upsilon_{rr} + p\upsilon_{rr} + p - 1)}{\upsilon_{rr} - \omega_{rr} + \omega_{SS} + p - 2p\upsilon_{rr} - p\omega_{rr} + p\upsilon_{rr} + 2p\omega_{rr} - p\omega_{SS} - 1}. \quad (eq.\ 10)$$

which simplifies to give $$\Phi_3 = \frac{1 - \upsilon_{rr}}{[(1 - \upsilon_{rr}) + (\omega_{rr} - \omega_{SS})]}. \quad (eq.\ 11)$$

Equivalence of Threshold Condition

Note, under the complete extremes of recessiveness and dominance, the threshold for fixation/extinction, $\Phi_3$, is the same. So provided $\Phi > \Phi_3$, the r allele will go to fixation regardless of whether the allele is fully recessive or fully dominant. However, the time taken to reach fixation will depend on the magnitude of $\Phi$.

Determinants of $\rho$ Equilibrium Stability

If the r allele is fully recessive with respect to the resistant phenotype, then $\omega_{Sr}=\omega_{SS}$ and so the lower threshold condition $\Phi_1$ (equation 4) equals 1 (provided $\upsilon_{Sr}<\upsilon_{SS}$) resulting in $\Phi_1 \geqq \Phi_2$ always being satisfied. Thus, recessiveness results in an unstable $\rho$ and the resistant allele will go to fixation if the proportion Bt exceeds the critical threshold $\Phi_3$.

If the r allele is dominant with respect to the resistant phenotype, then $\omega_{Sr}=\omega_{rr}$ and so the upper threshold $\Phi_2$ (equation 5) equals 1 (provided $\upsilon_{Sr}>\upsilon_{rr}$) and the lower limit $\Phi_1$ is less that 1 (as $\omega_{Sr}>\omega_{SS}$ by the definition of resistance) resulting in $\Phi_1<\Phi_2$ always being satisfied. Thus, dominance always results in a stable $\rho$ and the resistant allele will only to fixation if the proportion Bt exceeds the critical threshold $\Phi_2$.

Finally, if the r allele is partially dominant with respect to the resistant phenotype, then $\omega_{SS}<\omega_{Sr}<\omega_{rr}$ and either $\Phi_1<\Phi_2$ or $\Phi_1 \geqq \Phi_2$ may be satisfied, and so an intermediate stable equilibrium may, or may not, arise.

Note, high-dose refugia strategy, equates to recessive model in terms of resistant phenotype of heterozygote, i.e. $\omega_{Sr}=\omega_{SS}$. So $\rho$ is unstable and resistance will go to fixation if $\Phi > \Phi_3$. However, a low-dose strategy, equates to partial dominance model, i.e. $\omega_{SS}<\omega_{Sr}<\omega_{rr}$. And so depending on the details can get $0<\rho^*<1$.

EXAMPLE 2

RIDL Release

We assume that mass-reared males are released at a fixed ratio to the wild type population each generation (such that a proportion, $\alpha$, of the total population each generation is made up of released males). All male, engineered released males are assumed to be homozygous sensitive to Bt toxins, and also homozygous at one autosome for the RIDL construct. The transformed autosome containing RIDL is termed L, equivalent to untransformed autosome w in the wild population (see FIG. 2), which we assume is different to the autosome carrying the toxin sensitive locus (or, more generally, that the RIDL and Bt resistant loci are substantially unlinked).

We assume the RIDL construct also imposes a sex-specific fitness cost prior to sexual maturity, e.g. at a larval stage. Under the assumption of a random distribution of larvae across Bt and non-Bt crops, the average relative fitness, $\Omega$, of larvae of genotype i is $$\Phi_i = (1-\epsilon_i)[\omega_i \Phi + \upsilon_i(1-\Phi)]$$

where $\epsilon_i$ is the sex-specific, relative fitness cost imposed by RIDL and $\omega_i$ and $\upsilon_i$ are the relative fitness of larvae on Bt and non-Bt crops, respectively.

Figure 3:
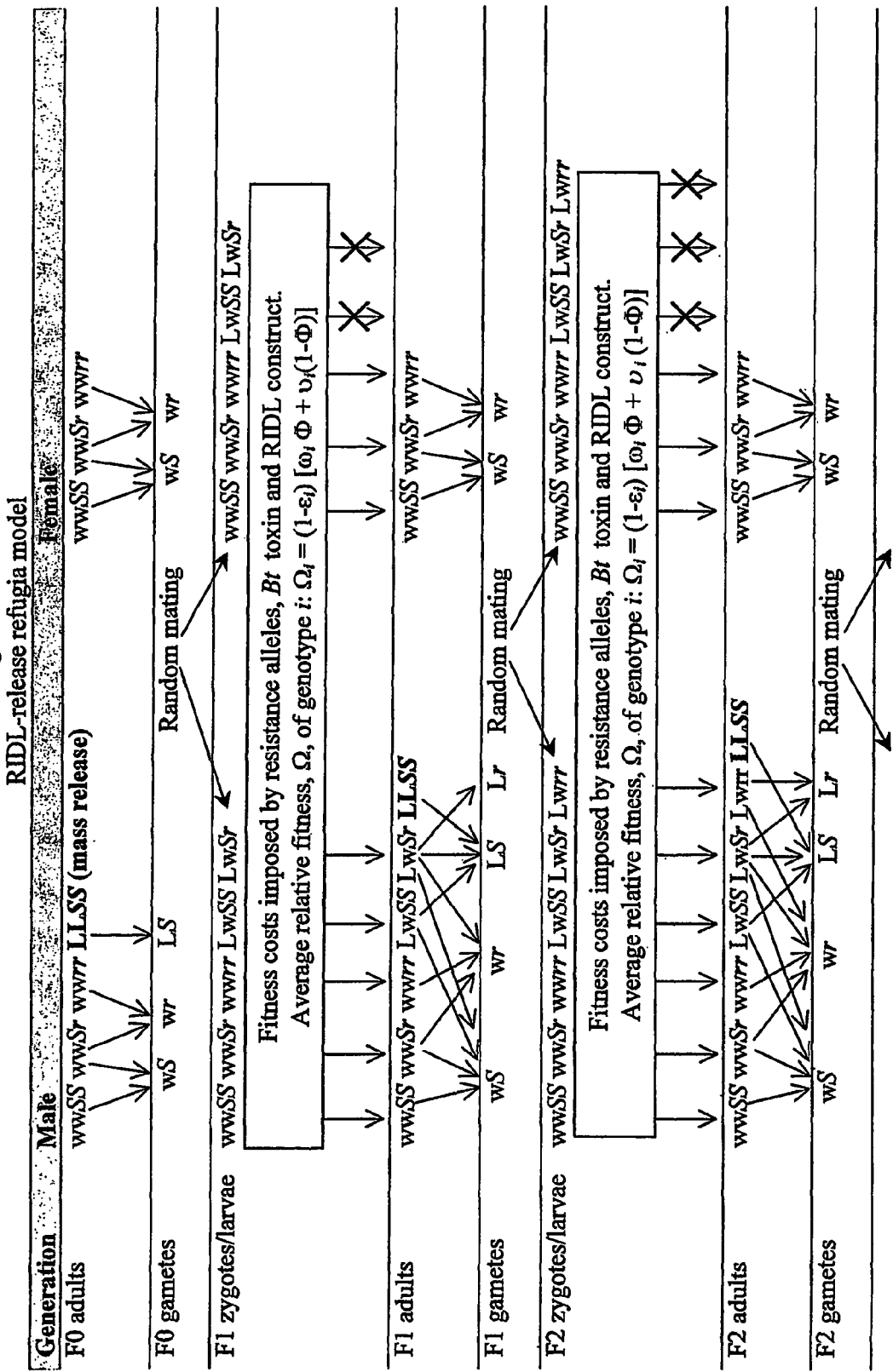
FIG. 3 shows a RIDL-release refugia model.

If RIDL were a fully dominant lethal, then for all female larvae containing RIDL $\epsilon_i=1$ and so average fitness $\Omega_i=0$. Under these conditions, as shown in FIG. 2 and FIG. 3, there are a total of seven male and three female viable genotypes (defined at the w/L autosome and S/r locus). Nine (six male and three female) genotypes resulting from matings in the field, while the tenth (LLSS) is the engineered RIDL release male. (Note, we can relax the $\epsilon=1$ assumption at the larval stage for females to allow some viable RIDL females to emerge; this obviously increases the number of viable genotypes up to 18–wwSS, wwSr, wwrr, LwSS, LwSr, Lwrr, LLSS, LLSr, LLrr both female and male).

The structure of the RIDL release model is essentially the same as that shown in FIG. 1 but adapted to include the different viable genotypes as shown in FIG. 3.

For any given set of assumptions about the relative fitness of the different genotypes on Bt-crops ($\omega_i$) and non-Bt crops ($\upsilon_i$), the fitness costs associated with RIDL in the larval stage ($\epsilon_i$) and the staring frequency of the resistant allele ($p_0$), we can compare the dynamics of the r allele frequency with and without RIDL release, for any combination of the proportion of crops expressing Bt ($\Phi$) and the release RIDL frequency ($\alpha$).

Model Outputs

Responsive Release

Figure 4:
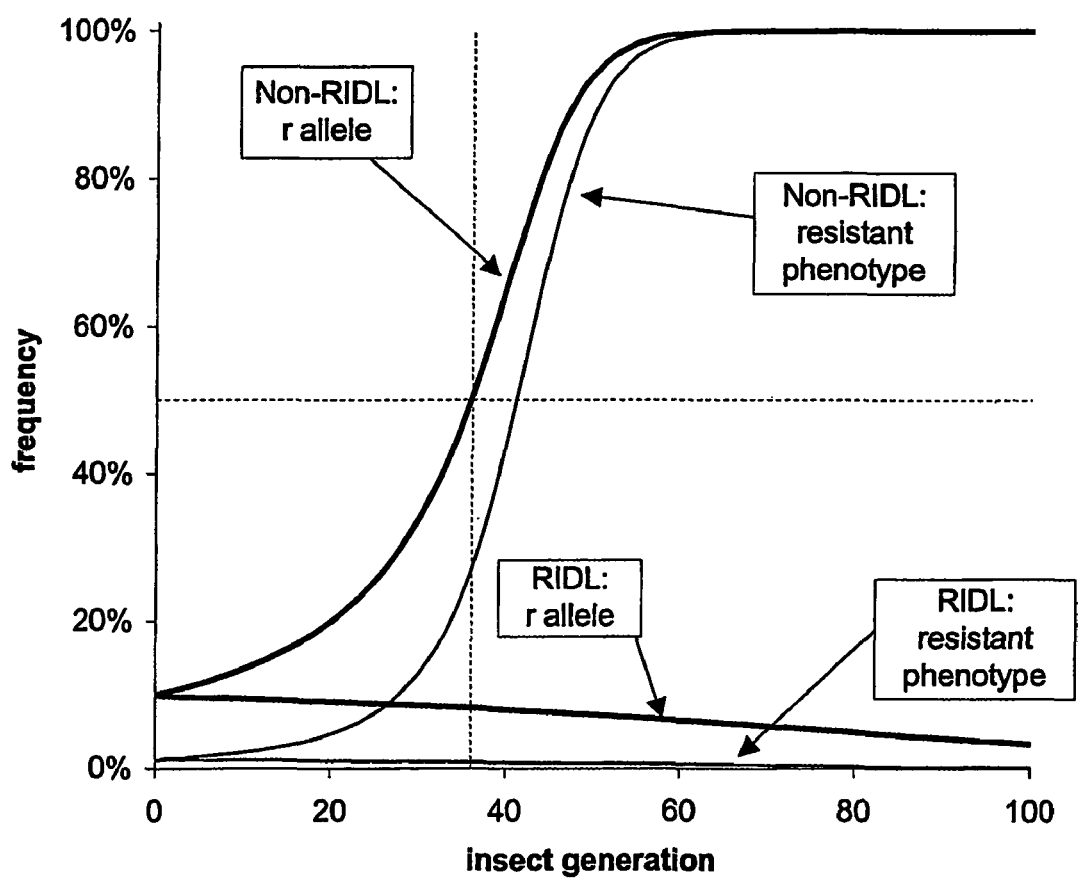
FIG. 4 is an example of the effects of a 1:10 RIDL release ratio on the evolution of resistance.
Figure 5:
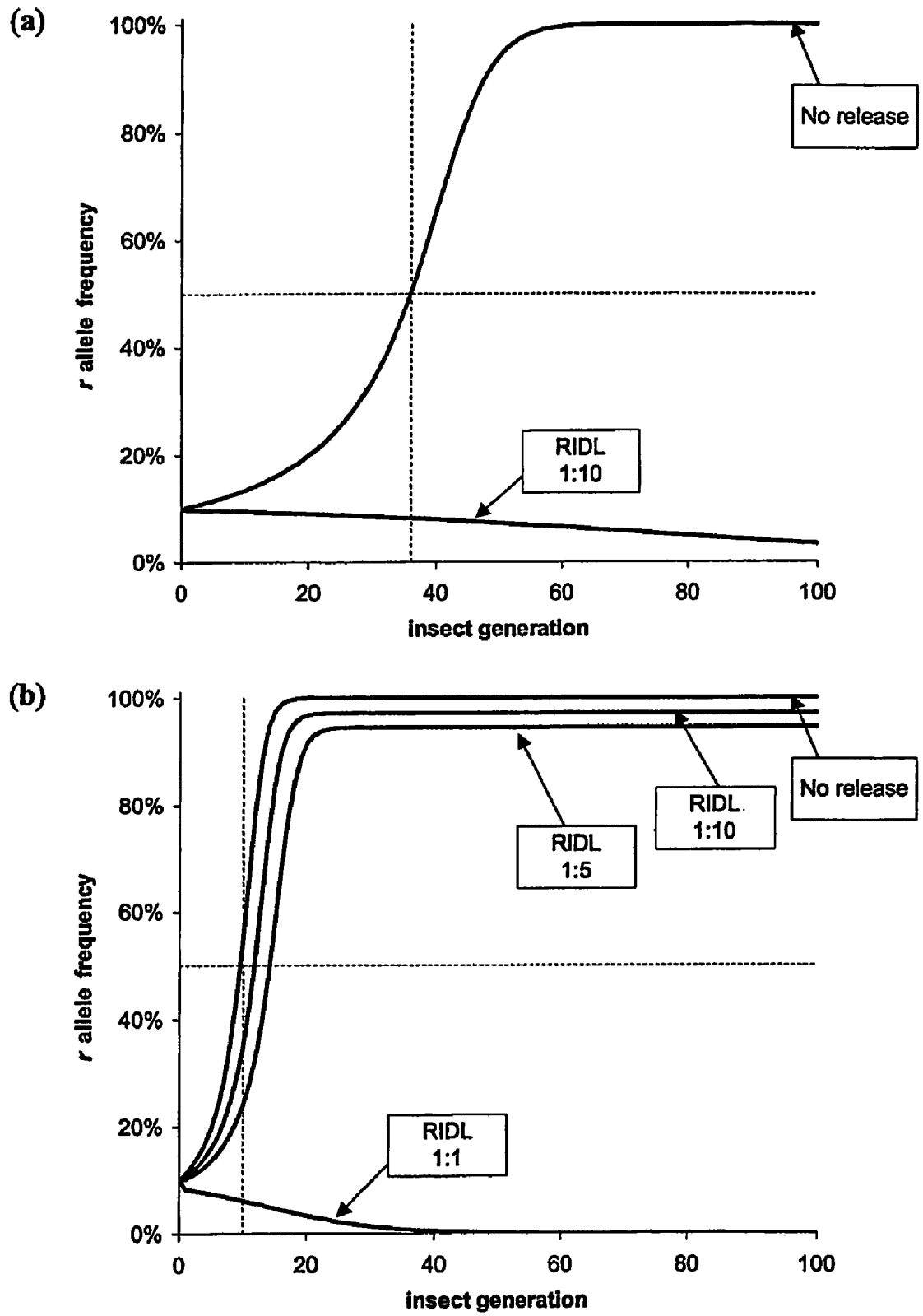
FIG. 5 shows different refuge sizes and the impact of different RIDL release ratios required to reduce the frequency of the r allele.

Releasing RIDL males always reduces the rate of spread of the r allele, even at very low release ratios (e.g. 1 RIDL release for every 10 wild types). We can formally quantify the effects of RIDL release strategies relative to a refuge only approach, by using the parameters defined by Carrière & Tabashnik (Carriàre, Y & Tabashnik, B E. 2001, Reversing insect adaptation to transgenic insecticidal plants. Proc. Roy. Soc. (Lond) B. 1475-80) in their examination of the effect of refugia on the management of resistance in agricultural pest populations. The results are shown in FIGS. 4 and 5 and Tables 2, 3 and 4.

TABLE 1

Parameter values used in quantifying the model outputs that allow comparison with the findings of Carrière & Tabashnik (2001).

| Variable | Value |
|---|---|
| Starting r allele frequencies in generation 0 | |
| $p_0$ | 0.1 |
| Relative fitness on non-Bt crops (v) | |
| $\upsilon_{SS}$ | 1 |
| $\upsilon_{Sr}$ | 1 |
| $\upsilon_{rr}$ | 0.7 or 0.4 |
| Relative fitness on Bt crops ($\omega$) | |
| $\omega_{SS}$ | 0 or 0.01 |
| $\omega_{Sr}$ | 0 or 0.01 |
| $\omega_{rr}$ | 0.1, 0.2 or 0.4 |
| Proportion Bt crops | |
| $\Phi$ | 0.5, 0.7, 0.9 or 0.99 |
| Sex-specific RIDL fitness cost in larvae ($\epsilon$) | |
| $\epsilon_{male}$ | 0.1 |
| $\epsilon_{female}$ | 1 |

FIG. 4 shows the effects of a 1:10 RIDL release ratio (i.e. 1 RIDL to 10 wild-types) and on the evolution of resistance. The parameter values are shown in Table 1, with $\upsilon_{Sr}=1$, $\upsilon_{rr}=0.4$, $\omega_{SS}=\omega_{Sr}=0$, $\omega_{rr}=0.1$, and a 10% refuge (i.e. $\Phi=0.9$). It can be seen that the frequency of the r allele reaches 0.5 in 36 generations in the non-RIDL refugia only scenario (as also predicted Carrière & Tabashnik, 2001). However, under the RIDL release scenario, even at a release ratio of 1:10, the spread of resistance is reversed. The phenotype frequencies, assuming the resistant trait is fully recessive, are also shown.

TABLE 2

Effect of a 1:10 release ratio per generation on the number of generations required for the r allele frequency to reach 0.5. Note, ∞ represents a decrease in the frequency of the r allele, i.e. a reversal of resistance. As with Carrière & Tabashnik, we assume that resistance was recessive (i.e. fitness of $v_{SS} = v_{Sr} = 1$ and $\omega_{SS} = \omega_{Sr} = 0$).
Other values, unless indicated below, are as in Table 1.

| | | Refuge, (1 − Φ) | | | | | |
|---|---|---|---|---|---|---|---|
| | | 0.1 | | 0.3 | | 0.5 | |
| $v_{rr}$ | $\omega_{rr}$ | Current | RIDL | Current | RIDL | Current | RIDL |
| 0.7 | 0.1 | 19 | 31* | ∞ | ∞ | ∞ | ∞ |
| 0.7 | 0.2 | 9 | 11* | 64 | ∞ | ∞ | ∞ |
| 0.7 | 0.4 | 5 | 6* | 18 | 28* | 104 | ∞ |
| 0.4 | 0.1 | 36 | ∞ | ∞ | ∞ | ∞ | ∞ |
| 0.4 | 0.2 | 11 | 13* | ∞ | ∞ | ∞ | ∞ |
| 0.4 | 0.4 | 5 | 6* | 33 | ∞ | ∞ | ∞ |

*Note,
r allele increases to a non-zero stable equilibrium level less than 1.

TABLE 3a and b

Effect of RIDL release at different release ratios on the number of generations required for the r allele frequency to reach 0.5 with (a) 10%, i.e. Φ = 0.9 and (b) 5%, i.e. Φ = 0.95 refuge. Other parameter assumptions are as in Tables 2.

| | | RIDL release ratio (RIDL males:wild-types) | | | | | |
|---|---|---|---|---|---|---|---|
| $v_{rr}$ | $\omega_{rr}$ | 0 | 1:10 | 1:5 | 1:1 | 10:1 | 50:1 |
| (a) | | | | | | | |
| 0.7 | 0.1 | 19 | 31* | 80* | ∞ | ∞ | ∞ |
| 0.7 | 0.2 | 9 | 11* | 12* | ∞ | ∞ | ∞ |
| 0.7 | 0.4 | 5 | 6* | 6* | 9* | ∞ | ∞ |
| 0.4 | 0.1 | 36 | ∞ | ∞ | ∞ | ∞ | ∞ |
| 0.4 | 0.2 | 11 | 13* | 16* | ∞ | ∞ | ∞ |
| 0.4 | 0.4 | 5 | 6* | 7* | 10* | ∞ | ∞ |
| (b) | | | | | | | |
| 0.7 | 0.1 | 9 | 10* | 12* | ∞ | ∞ | ∞ |
| 0.7 | 0.2 | 5 | 5* | 6* | 9* | ∞ | ∞ |
| 0.7 | 0.4 | 3 | 3* | 4* | 5* | 9* | 13* |
| 0.4 | 0.1 | 10 | 12* | 15* | ∞ | ∞ | ∞ |
| 0.4 | 0.2 | 5 | 6* | 6* | 9* | ∞ | ∞ |
| 0.4 | 0.4 | 3 | 4* | 4* | 5* | 9* | 13* |

*Note,
r allele increases to a non-zero stable equilibrium level less than 1.

TABLE 4

| | | RIDL release ratio (RIDL males:wild-types) | | | | | |
|---|---|---|---|---|---|---|---|
| $v_{rr}$ | $\omega_{rr}$ | 0 | 1:10 | 1:5 | 1:1 | 10:1 | 50:1 |
| 0.7 | 0.1 | 4 | 5* | 5* | 7* | 19* | >250 |
| 0.7 | 0.2 | 3 | 3* | 3* | 4* | 7* | 10* |
| 0.7 | 0.4 | 2 | 2* | 2* | 3* | 4* | 6* |
| 0.4 | 0.1 | 4 | 5* | 5* | 7* | 20* | ∞ |
| 0.4 | 0.2 | 3 | 3* | 3* | 4* | 7* | 10* |
| 0.4 | 0.4 | 2 | 2* | 2* | 3* | 4* | 6* |

*Note,
r allele increases to a non-zero stable equilibrium level less than 1.

Effect of RIDL release at different ratios on the number of generations required for the r allele frequency to reach 0.5 when the refuge size is only 1% (or (Φ=0.99), which may arise when all agricultural production in an area is with Bt crops but there is migration of pest of from outside the area, or some use of alternate host plants. We also assume that there is some small probability of survival of wild-type and heterozygous pest on transgenic crops (i.e. $\omega_{SS}=\omega_{Sr}=0.01$). Other parameter assumptions are as in Table 2. The results show the dilution effects of the RIDL release in the absence of a significant refuge. Note, significant effects on the growth of resistance are only seen at high release ratios at which point the RIDL-release strategy would be expected to have a major suppressive effect on the pest population. Also note that we are here analysing allele frequency; a highly effective Bt crop, especially when combined with RIDL releases, will also have a very strong effect on pest population size. This strong local suppression of the wild population is unlikely to affect the immigration rate as strongly, so the effective refuge size may increase, leading to a situation closer to that illustrated in Tables 3a and 3b.

It will be apparent that lowering the size of the refugia will increase the release ratio of male RIDL transgenic required to control the spread of the resistant allele. This is shown in FIGS. 5a and b.

FIGS. 5a and b show the different refuge sizes of (a) 10% (i.e. Φ=0.9), and (b) 5% (i.e. Φ=0.95) and the impact of different RIDL release ratios required to reduce the frequency of the r allele. All other parameters are as in FIG. 4. The RIDL to wild type release ratios are indicated on the graphs.

Figure 6:
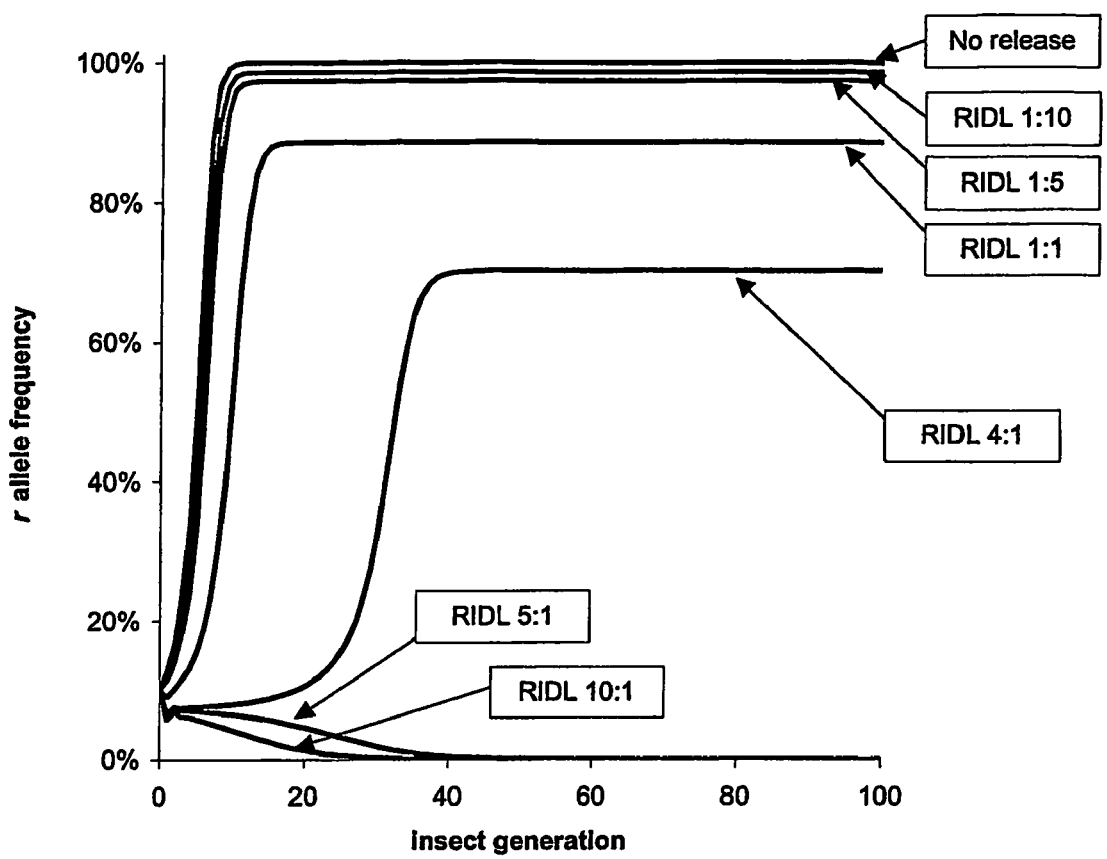
FIG. 6 illustrates the effect of RIDL release ratio.

The effect of RIDL release ratio is illustrated in FIG. 6. The release of RIDL susceptibles will in all cases reduce the rate of increase in the r allele. However, above a certain critical threshold the release will reverse the spread. In FIG. 6, the parameters are as in FIG. 4 except $\omega_{rr}$=0.4. The initial frequency of the r allele is 0.1 and the refuge size set at 10%. It can be seen that release ratios of around 5:1 or greater will reverse the spread of the resistant allele.

Prophylactic Release

Figure 7:
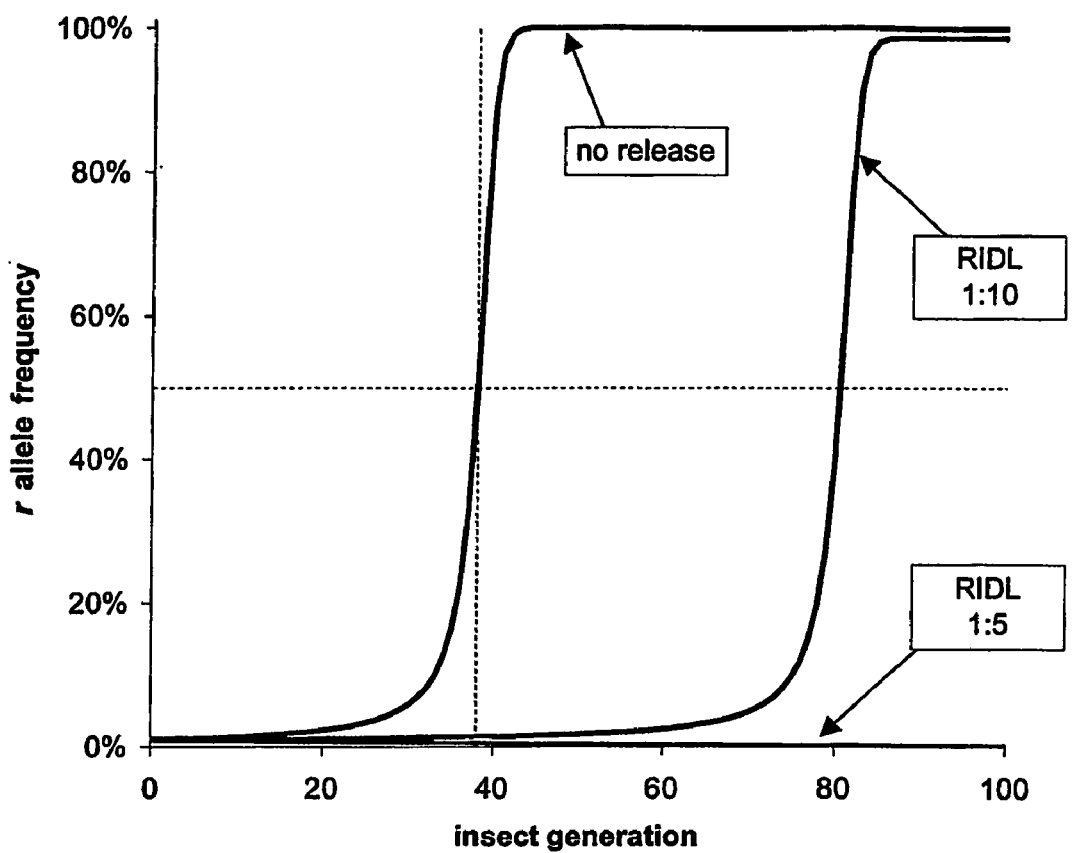
FIG. 7 illustrates the effects of starting resistant allele frequency.

At allele frequencies of around 5-10% or more, phenotypic resistance will be detectable through surveillance programmes and RIDL release programmes may be used in a responsive manner to control the spread of resistance. At lower allele frequencies, e.g. 1% or lower, phenotypic resistance will be unlikely to be detected by routine surveillance. However, RIDL-release may be used, for example, in a prophylactic manner to prevent development or spread of future resistance. The effects of different release ratios on the development of resistance in a pest population with a starting r allele frequency of 1% are shown in FIG. 7. It can be seen that, in contrast to FIG. 6, a release ratio as low as 1:10 will maintain the frequency of the r allele frequency below 50% for over 80 generations, while a release ratio of 1:5 (RIDL to wild types) is sufficient to pre vent the growth of resistance.

FIG. 7 shows the effects of starting resistant allele frequency. All parameter values are as in FIG. 6, apart from the starting r allele frequency which is 0.01.

Reversing Established Resistance

At the other extreme from prophylactic release, the invention can also be applied to reduce the level of well-established resistance in a pest population. For example, FIG. 8 shows the impact of different release ratios on the temporal trajectory of the resistant allele frequency from a starting level of 50%. The impact of the strategy is sensitive to the relative fitness of the homozygous resistant genotype on Bt-crops, the parameter $\omega_{rr}$, as shown in FIGS. 8a and b.

FIGS. 8a and b show reversing established resistance. In (a) $\omega_{rr}$=0.1 and in (b) $\omega_{rr}$=0.4. All other parameters are as in FIG. 4.

Synergistic Effects of Population Suppression and Resistance Dilution

As discussed earlier, release of transgenic males carrying a RIDL construct that confers female specific dominant lethality will result in population suppression, with the degree of suppression dependent on the release ratio and the ecology of the target population (e.g. basic reproductive number and degree of non-random mating). The analytical framework described above may be adapted to allow for changes in pest population numbers. Accordingly, the release of RIDL males may be defined in two ways (1) as a ratio of the population size in the generation of release (i.e. if the population size reduces, the number of released males is reduced, so that the ratio of released males to wild types remains constant) and (2) the ratio is defined in relation to the wild population size in generation 0 (i.e. the total number of RIDL released males remains constant regardless of changes in the target population size). The latter strategy is closer to the actual practice of SIT programmes. In the absence of any RIDL release the growth rate of the target population is defined by the basic reproductive number, $R_0$, defined as the number of female offspring per female.

Figure 9:
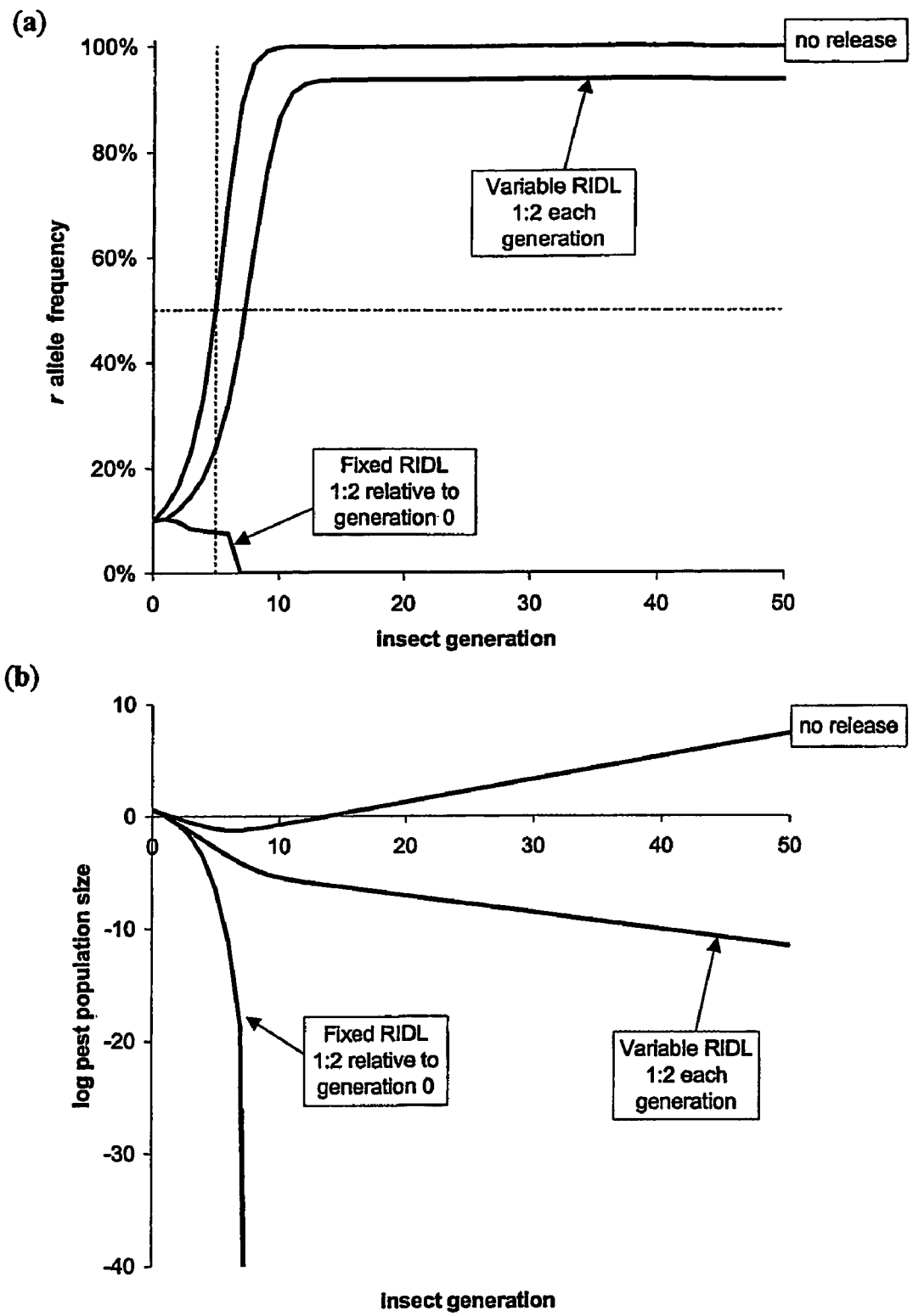
FIG. 9 illustrates the simultaneous effects of RIDL release on (a) resistance dilution and (b) population suppression under two different RIDL release strategies.

It is apparent that the resistance dilution effects of RIDL release are dramatically more favourable when the population suppression effects under the fixed RIDL release scenario are simultaneously accounted for. This is illustrated in FIG. 9, which shows the simultaneous effects of RIDL release on (a) resistance dilution and (b) population suppression under two different RIDL release strategies—variable release in which the ratio is constant to the population size in each generation and fixed release in which the ratio is constant relative to the population size in generation 0. The parameter values are as in FIG. 6. The $R_0$ of the pest population is 4 and no density dependence is assumed.

The invention claimed is:

1. A method of controlling a target insect population capable of sexual reproduction, the method comprising:
    inhibiting or reversing of the spread, in a target insect population, of a first genetic, non wild type, pesticide-resistance trait, by introducing sexually compatible individuals substantially homozygous for a wild type, sensitive counterpart of the resistance trait into the target insect population, wherein a heterozygote form of the resistance trait having an associated reduced level of fitness by comparison with the resistant homozygotes in the presence of a pesticide, and both the heterozygote and resistant homozygote forms having an associated reduced level of fitness by comparison with the sensitive homozygote counterpart form in the absence of the pesticide; and
    treating with the pesticide and using refugia to permit survival of non resistant members of the population.

2. The method according to claim 1, wherein the members of the population are selected from the group consisting of: Australian sheep blowfly (*Lucilia cuprina*), New world screwworm (*Cochliomyia hominivorax*), Old World Screwworm (*Chrysomya bezziana*), Tsetse fly (*Glossina*spp), Stable Fly (*Stomoxys calcitrans*), Face Fly (*Musca autumnalis*), Horn Fly (*Haematoba irritans*) Asian tiger mosquito (*Aedes albopictus*), yellow fever mosquito (*Aedes aegypti*), malaria mosquitoes, e.g. (*Anopheles gambiae, Anopheles Stephens, Anopheles funestus, Anopheles arabiensis, Anopheles dirus*. Other mosquito vectors of disease, e.g. (*Culex pipiens, Culex quinquefasciatus*), Japanese beetle (*Popilla japonica*), White-fringed beetle (*Graphognatus*spp.), Boll weevil (*Anthonomus grandis*), Corn Rootworms: Western (*Diabrotica virgifera virgifera*), Northern (*Diabrotica barberi*), Southern (*Diabrotica undecimpunctata howardi*) and Mexican (*D. virgifera zeae*), Red Palm Weevil (*Rhynchophorus ferrugineus*), Sweet potato Weevils (*Cylas formicarius, eucepes postfasciatus*), Colorado beetle (*Leptinotarsa decemlineata*), Pine Shoot Beetle (*Tomicus piniperda*), Mahogany Shoot Borer (*Hypsipyla robusta*), Flour Beetle (*Tribolium confusum*), Pea Weevil (*Bruchus pisorum*), Grain borers (*Prostefanus truncatus, Rhyzopertha dominica*), Flat grain beetle (*Cryptolestes ferrugineus*), Granary & Rice Weevils (*Cytophilus*spp.), Citrus blackfly (*Aleurocanthus woglumi*), Oriental fruit fly (*Dacus dorsalis*), Olive fruit fly (*Dacus oleae*), tropical fruit fly (*Dacus cucurbitae, Dacus zonatus*), Mediterranean fruit fly (*Ceratitis capitata*), Natal fruit fly (*Ceratitis rosa*), Cherry fruit fly (*Rhagoletis cerasi*), Queensland fruit fly (*Bactrocera tryoni*), Caribbean fruit fly (*Anastrepha suspensa*), Carambola Fruit Fly (*Bactrocera carambolae*), Mexican Fruit Fly (*Anastrepha ludens*), Onion Fly (*Delia antiqua*), Mushroom flies (*Lycoriella mali, Lycoriella auripila* & *Megaselia*spp.), Other fruit flies (*Tephritidae*), Gypsy moth (*Lymantria dispar*), Codling moth (*Cydia pomonella*), Brown tail moth (*Euproctis chrysorrhoea*), rice stem borer (*Tryporyza incertulas*), Pink Bollworm (*Pectinophora gossypiella*), Navel Orangeworm (*Amyelois transitella*), Peach twig worm (*Anarsia lineatella*), Painted Apple Moth (*Teia anartoides*), Corn Earworm (*Helicoverpa armigera, Helicoverpa zea*), Tobacco Budworm (*Heliothis virescens*--and other Heliothines), Tobacco Hornworm (*Maduca sexta*), Potato Tuber Moth (*Phthorimaea operclella*), Date Moth (*Ectomyelois ceratoniae*), Oriental Fruit Moth (*Grapholita molesta*), Diamondback moth (*Plutella xylostella*), Indian Meal Moth (*Plodia interpunctella*), Greenhouse Whiteflies (e.g. *Bemisia tabaci, Trialeurodes vaporarium*), Cattle Fever tick (*Boophilus microplus*), and other ticks of veterinary importance and Psocids (*Liposcelis*spp.).

3. The method according to claim 2, wherein the targeted population is malaria mosquitoes.

4. The method according to claim 2, wherein the targeted population is medfly.

5. The method according to claim 1, wherein the genetic trait to be inhibited or reversed comprises multiple alleles.

6. The method according to claim 1, for the inhibition or reversal of multiple genetic traits.

7. The method according to claim 1, comprising providing said refugia to permit survival of non resistant members of the population.

8. The method according to claim 1, wherein the pesticide is a chemical pesticide.

9. The method according to claim 1, wherein the pesticide is expressed by a food crop.

10. The method according to claim 9, wherein the pesticide is *Bacillus thuringiensis*toxin expressed by the food crop.

11. The method according to claim 9, wherein the refugia are provided by individual plants forming the food crop.

12. The method according to claim 1, wherein the numbers of individuals introduced are calculated to inhibit a trait developing in a population which is substantially free from the trait.

13. The method according to claim 1, wherein the numbers of individuals introduced are 10% or less of the population.

14. The method according to claim 1, wherein the numbers of individuals introduced are calculated to reverse a trait already present in a population.

15. The method according to claim 1, wherein the numbers of individuals introduced are at least equal to the numbers of individuals in the population.

16. The method according to claim 1, wherein the individuals carrying the counterpart also carry a further trait conferred on heterozygotes and/or homozygotes therefor.

17. The method according to claim 16, wherein the further trait is inability to diapause or refractoriness to a pathogen.

18. The method according to claim 1, wherein the individuals released into the target population are transgenics modified to carry a second trait which is dominant lethal or which results in reduced average fitness in at least one subsequent generation.

19. The method according to claim 18, wherein said fitness associated with said second trait is not zero for the immediately subsequent generation.

20. The method according to claim 18, wherein the second trait confers a reduced level of fitness on individuals carrying that trait in either the heterozygous or homozygous form.

21. The method according to claim 18, wherein said second trait is substantially not linked to the counterpart.

22. The method according to claim 21, wherein the suppressor is substantially not linked to the second trait.

23. The method according to claim 21, wherein the suppressor is linked to the counterpart of the trait to be inhibited or reversed.

24. The method according to claim 18, wherein the introduced individuals are homozygous for both the second trait and a suppressor therefor.

25. The method according to claim 18, wherein the second trait is a dominant lethal.

26. The method according to claim 18, wherein the second trait is selective for females.

27. The method according to claim 18, wherein the dominant lethal gene is controlled by environmental conditions, diurnal rhythm or dietary components.

28. The method according to claim 27, wherein the dominant lethal gene is controlled by tetracycline.

29. The method according to claim 18, wherein the dominant lethal gene is sex-specific.

30. A method of controlling a target insect population capable of sexual reproduction, the method comprising:
    inhibiting or reversing the spread, in a target insect population of a first genetic, non wild type trait, by introducing sexually compatible individuals substantially homozygous for a wild type, sensitive counterpart of the resistance trait into the target insect population, wherein said first trait confers resistance to a pesticide or tolerance to predators, viruses, parasites or parasitoids; a heterozygote form of the resistance trait having an associated reduced level of fitness by comparison with the resistant homozygotes in the presence of pesticide, predator, virus, parasite or parasitoid, and both the heterozygote and resistant homozygote forms having an associated reduced level of fitness by comparison with the sensitive homozygote counterpart form in the absence of the pesticide, predator, virus, parasite or parasitoid; and
    treating with the pesticide, or application of the predator, virus, parasite or parasitoid, and use of refugia to permit survival of non resistant members of the population.

31. The method according to claim 30, wherein the individuals released into the target insect population are transgenics modified to carry a second trait which is dominant lethal or which results in reduced average fitness in at least one subsequent generation.

* * * * *